United States Patent
Gallichan et al.

(10) Patent No.: US 9,327,021 B2
(45) Date of Patent: May 3, 2016

(54) IMMUNOGENIC COMPOSITIONS

(75) Inventors: Scott Gallichan, Burlington (CA);
Ausra Mancevski, Toronto (CA);
Nathalie Reveneau, Toronto (CA); Jin Su, Markham (CA); Francois Dalencon, Lyons (FR); Jean Haensler, Grezieu-la-Varenne (FR)

(73) Assignees: Sanofi Pasteur Limited, Toronto (CA); Sanofi Pasteur S.A., Lyons (FR)

( * ) Notice: Subject to any disclaimer, the term of this patent is extended or adjusted under 35 U.S.C. 154(b) by 0 days.

(21) Appl. No.: 13/885,485

(22) PCT Filed: Nov. 15, 2011

(86) PCT No.: PCT/CA2011/050705
§ 371 (c)(1),
(2), (4) Date: Sep. 12, 2013

(87) PCT Pub. No.: WO2012/065263
PCT Pub. Date: May 24, 2012

(65) Prior Publication Data
US 2013/0344109 A1    Dec. 26, 2013

Related U.S. Application Data

(60) Provisional application No. 61/413,699, filed on Nov. 15, 2010.

(51) Int. Cl.
*A61K 6/00* (2006.01)
*A61K 39/39* (2006.01)
(Continued)

(52) U.S. Cl.
CPC .............. *A61K 39/39* (2013.01); *A61K 9/0019* (2013.01); *A61K 9/107* (2013.01); *A61K 9/1075* (2013.01);
(Continued)

(58) Field of Classification Search
None
See application file for complete search history.

(56) References Cited

U.S. PATENT DOCUMENTS

2003/0219453 A1* 11/2003 Maisonneuve et al. .... 424/190.1
2007/0014805 A1    1/2007 Dalencon et al.
(Continued)

FOREIGN PATENT DOCUMENTS

WO    WO 2009056535 A2 *  5/2009
WO    PCT/CA2011/050705     5/2013

OTHER PUBLICATIONS

Igietseme et al. 2000 (Induction of Protective Immunity against Chlamydia trachomatis Genital Infection by a Vaccine Based on Major Outer Memberan Prtoein-Lipophilic Immune Response-Stimulating Complexes; Infection and Immunity, 6798-6806).*
(Continued)

*Primary Examiner* — Gary Nickol
*Assistant Examiner* — Mary Lyons
(74) *Attorney, Agent, or Firm* — Patrick J. Halloran

(57) ABSTRACT

The present invention provides compositions comprising a Chlamydial major outer membrane protein (referenced herein as "MOMP"), from at least one Chlamydial serovar and an adjuvant, characterized in that the adjuvant comprises the product E6020 having CAS Number 287180-63-6. The composition may further comprise at least one carrier system (e.g., emulsion, mineral particle). The MOMP protein may be derived from any species of *Chlamydia* (e.g., *C. trachomatis, C. pneumoniae, C. psittaci*, or *C. trachomatis* MoPn). In preferred embodiments, the composition comprises one or more major outer membrane proteins each derived from different serovars of *C. trachomatis*. The invention also provides methods of inducing an immune response to a *Chlamydia* species (e.g., *C. trachomatis*) in a subject, by administering to the subject a composition of the invention.

17 Claims, 2 Drawing Sheets

Figure 1:
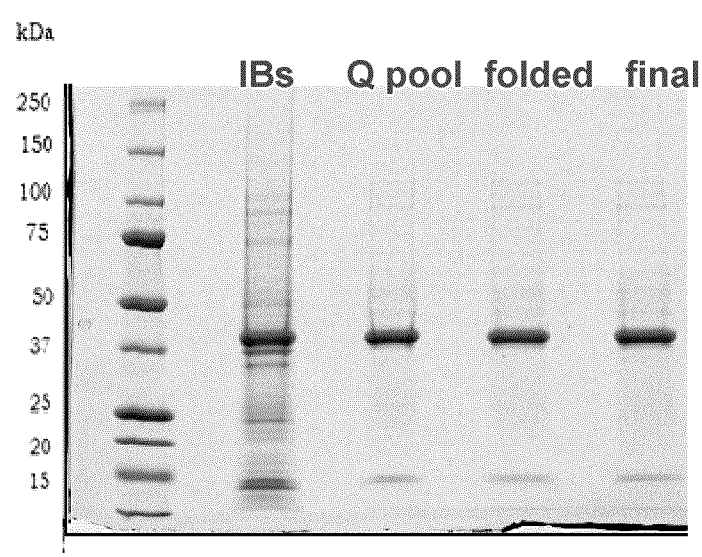

Blue Native PAGE gel analysis of pilot scale (left, A,B) and three lab scale (right, C-H) Ser E MOMP protein samples.

A,B: 10&15 µg respectively of pilot lot JR3182 Ser E MOMP
C,D: 5&10 µg respectively of lab scale lot JR3081
E,F: 5&10 µg respectively of lab scale lot JR3095
G,H: 5&10 µg respectively of lab scale lot JR3097

(51) Int. Cl.
  *A61K 38/00* (2006.01)
  *A61K 39/02* (2006.01)
  *A61K 9/00* (2006.01)
  *A61K 9/107* (2006.01)
  *A61K 39/118* (2006.01)
  *A61K 47/44* (2006.01)
  *A61K 39/00* (2006.01)

(52) U.S. Cl.
  CPC ............... *A61K 39/118* (2013.01); *A61K 47/44* (2013.01); *A61K 2039/55561* (2013.01); *A61K 2039/55566* (2013.01)

(56) References Cited

U.S. PATENT DOCUMENTS

| | | | |
|---|---|---|---|
| 2007/0082875 | A1 | 4/2007 | Fang et al. |
| 2009/0304739 | A1 | 12/2009 | Rappuoli et al. |
| 2009/0304742 | A1 | 12/2009 | Contorni |
| 2011/0110974 | A1 | 5/2011 | Depla et al. |

OTHER PUBLICATIONS

Baudner et al. 2009 (MF59 Emulsion is an Effective Delivery System for a Synthetic TLR4 agonist E6020; Pharmaceutical Research, 26(6):1477-1485).*

Su et al. 1995 (Protective efficacy of a parenterally administered MOMP-derived synthetic oligopeptide vaccine in a murine model of Chlamydia trachomatis genital tract infection: serum neutralizing IgG antibodies do not protect against chlamydial genital tract infection; Vaccine 13(11):1023-1032).*

Baudner, et al. MF59 is an Effective Delivery System for a Synthetic TLR4 Agonist (E6020). Pharm Res. 26(6): 1477-1485 (2009).

Caldwell, et al. Purification and Partial Characterization of the Major Outer Membrane Protein of Chlamydia trachomatis. Inf. Immun. 31(3): 1161-1176 (1981).

Hawkins, et al. A Novel Class of Endotoxin Receptor Agonists with Simplified Structure, Toll-Like Receptor 4-Dependent Immunostimulatory Action, and Adjuvant Activity. J. Pharm. Exp. Ther. 300(2): 655-661 (2002).

Igietseme, et al. Induction of Protective Immunity against Chlamydia trachomatis Genital Infection by a Vaccine Based on Major Outer Membrane Protein-Lipophilic Immune Response-Stimulating Complexes. Inf. Immun. 68(12): 6798-6806 (2000).

Li, et al. Induction of Cross-Serovar Protection against Genital Chlamydial Infection by a Targeted Multisubunit Vaccination Approach. Clin. Vaccine Immunol. 14(12): 1537-1544 (2007).

Morefield, et al. Synthetic Toll-Like Receptor 4 Agonist Enhances Vaccine Efficacy in an Experimental Model of Toxic Shock Syndrome. Clin. Vaccine Immunol. 14(11): 1499-1504 (2007).

Pal, et al. Vaccination with the Chlamydia trachomatis Major Outer Membrane Protein Can Elicit an Immune Response as Protective as That Resulting from Inoculation with Live Bacteria. Inf. Immun. 73(12): 8153-8160 (2005).

Su, et al. Protective Efficacy of a Parenterally Administered MOMP-derived Synthetic Oligopeptide Vaccine in a Murine Model of Chlamydia trachomatis Genital Tract Infection: Serum Neutralizing IgG Antibodies Do Not Protect Against Chlamydial Genital Tract Infection. Vaccine. 13(11): 1023-1032 (1995).

* cited by examiner

FIGURE 2 Blue Native PAGE gel analysis of pilot scale (left, A,B) and three lab scale (right, C-H) Ser E MOMP protein samples.
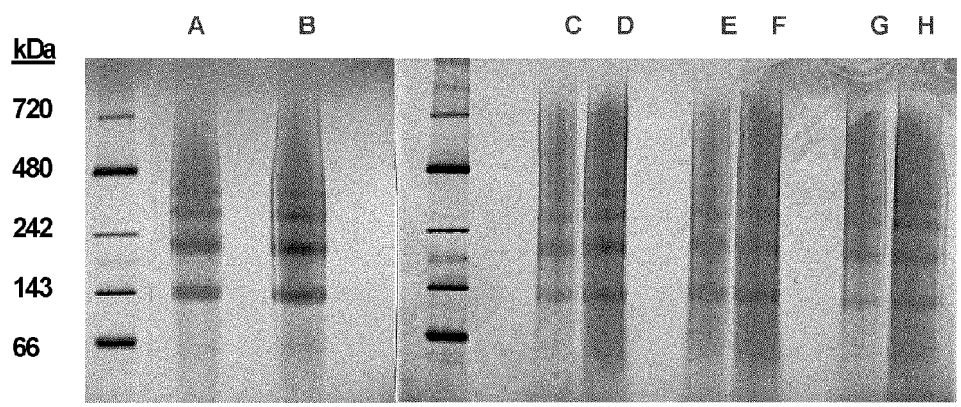
A,B: 10&15 μg respectively of pilot lot JR3182 Ser E MOMP
C,D: 5&10 μg respectively of lab scale lot JR3081
E,F: 5&10 μg respectively of lab scale lot JR3095
G,H: 5&10 μg respectively of lab scale lot JR3097

SEQUENCE LISTING

<160> NUMBER OF SEQ ID NOS: 11

<210> SEQ ID NO 1
<211> LENGTH: 1116
<212> TYPE: DNA
<213> ORGANISM: Chlamydia trachomatis

<400> SEQUENCE: 1

| | | |
|---|---|---|
| atgcctgtgg ggaatcctgc tgaaccaagc cttatgatcg acggaattct gtgggaaggt | 60 |
| ttcggcggag atccttgcga tccttgcacc acttggtgtg acgctatcag catgcgtatg | 120 |
| ggttactatg gtgactttgt tttcgaccgt gttttgaaaa cagatgtgaa taagaattc | 180 |
| caaatgggtg acaagcctac aagtactaca ggcaatgcta cagctccaac cactcttaca | 240 |
| gcaagagaga atcctgctta cggccgacat atgcaggatg ctgagatgtt tacaaatgcc | 300 |
| gcttgcatgg cattgaatat ttgggatcgc tttgatgtat tctgtacact aggagcctct | 360 |
| agcggatacc ttaaaggaaa ctctgcttct ttcaatttag ttggattgtt tggagataat | 420 |
| gaaaatcaaa gcacggtcaa aacgaattct gtaccaaata tgagcttaga tcaatctgtt | 480 |
| gttgaacttt acacagatac tgccttctct tggagcgtgg gcgctcgagc agctttgtgg | 540 |
| gagtgcggat gtgcgacttt aggggcttct ttccaatacg ctcaatctaa acctaaagtc | 600 |
| gaagaattaa acgttctctg taacgcagct gagtttacta tcaataagcc taaggatat | 660 |
| gtagggcaag aattccctct tgcactcata gcaggaactg atgcagcgac gggcactaaa | 720 |
| gatgcctcta ttgattacca tgagtggcaa gcaagtttag ctctctctta cagattgaat | 780 |
| atgttcactc cctacattgg agttaaatgg tctcgagcaa gttttgatgc cgatacgatt | 840 |
| cgtatagccc agccaaaatc agctacagct atctttgata ctaccacgct taacccaact | 900 |
| attgctggag ctggcgatgt gaaagctagc gcagagggtc agctcggaga taccatgcaa | 960 |
| atcgtctcct tgcaattgaa caagatgaaa tctagaaaat cttgcggtat tgcagtagga | 1020 |
| acgactattg tagatgcaga caaatacgca gttacagttg agactcgctt gatcgatgag | 1080 |
| agagctgctc acgtaaatgc acaattccgc ttctaa | 1116 |

<210> SEQ ID NO 2
<211> LENGTH: 371
<212> TYPE: PRT
<213> ORGANISM: Chlamydia trachomatis

<400> SEQUENCE: 2

Met Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Gln Met Gly Asp
    50                  55                  60

Lys Pro Thr Ser Thr Thr Gly Asn Ala Thr Ala Pro Thr Thr Leu Thr
65                  70                  75                  80

Ala Arg Glu Asn Pro Ala Tyr Gly Arg His Met Gln Asp Ala Glu Met
                85                  90                  95

Phe Thr Asn Ala Ala Cys Met Ala Leu Asn Ile Trp Asp Arg Phe Asp
            100                 105                 110

Val Phe Cys Thr Leu Gly Ala Ser Ser Gly Tyr Leu Lys Gly Asn Ser
        115                 120                 125

```
Ala Ser Phe Asn Leu Val Gly Leu Phe Gly Asp Asn Glu Asn Gln Ser
    130                 135                 140
Thr Val Lys Thr Asn Ser Val Pro Asn Met Ser Leu Asp Gln Ser Val
145                 150                 155                 160
Val Glu Leu Tyr Thr Asp Thr Ala Phe Ser Trp Ser Val Gly Ala Arg
                165                 170                 175
Ala Ala Leu Trp Glu Cys Gly Cys Ala Thr Leu Gly Ala Ser Phe Gln
            180                 185                 190
Tyr Ala Gln Ser Lys Pro Lys Val Glu Glu Leu Asn Val Leu Cys Asn
        195                 200                 205
Ala Ala Glu Phe Thr Ile Asn Lys Pro Lys Gly Tyr Val Gly Gln Glu
    210                 215                 220
Phe Pro Leu Ala Leu Ile Ala Gly Thr Asp Ala Ala Thr Gly Thr Lys
225                 230                 235                 240
Asp Ala Ser Ile Asp Tyr His Glu Trp Gln Ala Ser Leu Ala Leu Ser
                245                 250                 255
Tyr Arg Leu Asn Met Phe Thr Pro Tyr Ile Gly Val Lys Trp Ser Arg
            260                 265                 270
Ala Ser Phe Asp Ala Asp Thr Ile Arg Ile Ala Gln Pro Lys Ser Ala
        275                 280                 285
Thr Ala Ile Phe Asp Thr Thr Leu Asn Pro Thr Ile Ala Gly Ala
    290                 295                 300
Gly Asp Val Lys Ala Ser Ala Glu Gly Gln Leu Gly Asp Thr Met Gln
305                 310                 315                 320
Ile Val Ser Leu Gln Leu Asn Lys Met Lys Ser Arg Lys Ser Cys Gly
                325                 330                 335
Ile Ala Val Gly Thr Thr Ile Val Asp Ala Asp Lys Tyr Ala Val Thr
            340                 345                 350
Val Glu Thr Arg Leu Ile Asp Glu Arg Ala Ala His Val Asn Ala Gln
        355                 360                 365
Phe Arg Phe
    370

<210> SEQ ID NO 3
<211> LENGTH: 1122
<212> TYPE: DNA
<213> ORGANISM: Chlamydia trachomatis

<400> SEQUENCE: 3
atgcctgtgg ggaatcctgc tgaaccaagc cttatgatcg acggaattct gtgggaaggt      60
ttcggcggag atccttgcga tccttgcacc acttggtgtg acgctatcag catgcgtatg     120
ggttactatg gtgactttgt tttcgaccgt gttttgaaaa cagatgtgaa taaagagttt     180
gaaatgggcg aggctttagc cggagcttct gggaatacga cctctactct ttcaaaattg     240
gtagaacgaa cgaaccctgc atatggcaag catatgcaag acgcagagat gtttaccaat     300
gccgcttgca tgacattgaa tatttgggat cgttttgatg tattctgtac attaggagcc     360
accagtggat atcttaaagg aaattcagca tctttcaact tagttgggtt attcggcgat     420
ggtgtaaacg ccacgaaacc tgctgcagat agtattccta acgtgcagtt aaatcagtct     480
gtggtggaac tgtatacaga tactactttt gcttggagtg ttggagctcg tgcagctttg     540
tgggaatgtg gatgtgcaac tttaggagct tcttttccaat atgctcaatc taaacctaaa     600
atcgaagaat taaacgttct ctgtaacgca gcagagtttac tattaataa acctaaaggg     660
tatgtaggta aggagtttcc tcttgatctt acagcaggaa cagatgcagc gacgggcact     720
```

-continued

```
aaagatgcct ctattgatta ccatgagtgg caagcaagtt tatctctttc ttacagactc     780
aatatgttca ctccctacat tggagttaaa tggtctcgtg caagctttga ttctgataca     840
attcgtatag cccagccgag gttggtaaca cctgttgtag atattacaac ccttaaccca     900
actattgcag gatgcggcag tgtagctgga gctaacacgg aaggacagat atctgataca     960
atgcaaatcg tctccttgca attgaacaag atgaaatcta gaaaatcttg cggtattgca    1020
gtaggaacaa ctattgtgga tgcagacaaa tacgcagtta cagttgagac tcgcttgatc    1080
gatgagagag ctgctcacgt aaatgcacaa ttccgcttct aa                       1122
```

<210> SEQ ID NO 4
<211> LENGTH: 373
<212> TYPE: PRT
<213> ORGANISM: Chlamydia trachomatis

<400> SEQUENCE: 4

```
Met Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Glu Met Gly Glu
    50                  55                  60

Ala Leu Ala Gly Ala Ser Gly Asn Thr Thr Ser Thr Leu Ser Lys Leu
65                  70                  75                  80

Val Glu Arg Thr Asn Pro Ala Tyr Gly Lys His Met Gln Asp Ala Glu
                85                  90                  95

Met Phe Thr Asn Ala Ala Cys Met Thr Leu Asn Ile Trp Asp Arg Phe
            100                 105                 110

Asp Val Phe Cys Thr Leu Gly Ala Thr Ser Gly Tyr Leu Lys Gly Asn
        115                 120                 125

Ser Ala Ser Phe Asn Leu Val Gly Leu Phe Gly Asp Gly Val Asn Ala
    130                 135                 140

Thr Lys Pro Ala Ala Asp Ser Ile Pro Asn Val Gln Leu Asn Gln Ser
145                 150                 155                 160

Val Val Glu Leu Tyr Thr Asp Thr Thr Phe Ala Trp Ser Val Gly Ala
                165                 170                 175

Arg Ala Ala Leu Trp Glu Cys Gly Cys Ala Thr Leu Gly Ala Ser Phe
            180                 185                 190

Gln Tyr Ala Gln Ser Lys Pro Lys Ile Glu Glu Leu Asn Val Leu Cys
        195                 200                 205

Asn Ala Ala Glu Phe Thr Ile Asn Lys Pro Lys Gly Tyr Val Gly Lys
    210                 215                 220

Glu Phe Pro Leu Asp Leu Thr Ala Gly Thr Asp Ala Ala Thr Gly Thr
225                 230                 235                 240

Lys Asp Ala Ser Ile Asp Tyr His Glu Trp Gln Ala Ser Leu Ser Leu
                245                 250                 255

Ser Tyr Arg Leu Asn Met Phe Pro Tyr Ile Gly Val Lys Trp Ser
            260                 265                 270

Arg Ala Ser Phe Asp Ser Asp Thr Ile Arg Ile Ala Gln Pro Arg Leu
        275                 280                 285

Val Thr Pro Val Val Asp Ile Thr Thr Leu Asn Pro Thr Ile Ala Gly
    290                 295                 300
```

-continued

```
Cys Gly Ser Val Ala Gly Ala Asn Thr Glu Gly Gln Ile Ser Asp Thr
305                 310                 315                 320

Met Gln Ile Val Ser Leu Gln Leu Asn Lys Met Lys Ser Arg Lys Ser
                325                 330                 335

Cys Gly Ile Ala Val Gly Thr Thr Ile Val Asp Ala Asp Lys Tyr Ala
            340                 345                 350

Val Thr Val Glu Thr Arg Leu Ile Asp Glu Arg Ala Ala His Val Asn
        355                 360                 365

Ala Gln Phe Arg Phe
    370
```

<210> SEQ ID NO 5
<211> LENGTH: 1128
<212> TYPE: DNA
<213> ORGANISM: Chlamydia trachomatis

<400> SEQUENCE: 5

| | | |
|---|---|---|
| atgcctgtgg ggaatcctgc tgaaccaagc cttatgatcg acggaattct gtgggaaggt | 60 |
| ttcggtggag atccttgcga tccttgcacc acttggtgtg acgctatcag catgcgtatg | 120 |
| ggttactatg gtgactttgt tttcgaccgt gttttgaaaa cagatgtgaa taaagaattt | 180 |
| cagatgggag cggcgcctac taccagcgat gtagcaggct acaaaacga tccaacaaca | 240 |
| aatgttgctc gtccaaatcc cgcttatggc aaacacatgc aagatgctga atgtttacg | 300 |
| aacgctgctt acatggcatt aaatatctgg gatcgttttg atgtattttg tacattggga | 360 |
| gcaactaccg gttatttaaa aggaaactcc gcttccttca acttagttgg attattcgga | 420 |
| acaaaaacac aagcttctag ctttaataca gcgaatcttt tcctaacac tgctttgaat | 480 |
| caagctgtgg ttgagcttta tacagacact acctttgctt ggagcgtagg tgctcgtgca | 540 |
| gctctctggg aatgtgggtg tgcaacgtta ggagcttctt tccaatatgc tcaatctaaa | 600 |
| cctaaagtag aagagttaaa tgttctttgt aatgcatccg aatttactat taataagccg | 660 |
| aaaggatatg ttggggcgga atttccactt gatattaccg caggaacaga agctgcgaca | 720 |
| gggactaagg atgcctctat tgactaccat gagtggcaag caagtttagc cctttcttac | 780 |
| agattaaata tgttcactcc ttacattgga gttaaatggt ctagagtaag ttttgatgcc | 840 |
| gacacgatcc gtatcgctca gcctaaattg gctgaagcaa tcttggatgt cactactcta | 900 |
| aacccgacca tcgctggtaa aggaactgtg gtcgcttccg gaagcgaaaa cgacctggct | 960 |
| gatacaatgc aaatcgtttc cttgcagttg aacaagatga atctagaaa atcttgcggt | 1020 |
| attgcagtag gaacgactat tgtagatgca gacaaatacg cagttacagt tgagactcgc | 1080 |
| ttgatcgatg agagagcagc tcacgtaaat gcacaattcc gcttctaa | 1128 |

<210> SEQ ID NO 6
<211> LENGTH: 375
<212> TYPE: PRT
<213> ORGANISM: Chlamydia trachomatis

<400> SEQUENCE: 6

```
Met Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45
```

| | | | | | | | | | | | |
|---|---|---|---|---|---|---|---|---|---|---|---|
|Asp|Arg|Val|Leu|Lys|Thr|Asp|Val|Asn|Lys|Glu|Phe|Gln|Met|Gly|Ala|
| |50| | | |55| | | |60| | | | | | |

Ala Pro Thr Thr Ser Asp Val Ala Gly Leu Gln Asn Asp Pro Thr Thr
65                  70                  75                  80

Asn Val Ala Arg Pro Asn Pro Ala Tyr Gly Lys His Met Gln Asp Ala
                85                  90                  95

Glu Met Phe Thr Asn Ala Ala Tyr Met Ala Leu Asn Ile Trp Asp Arg
            100                 105                 110

Phe Asp Val Phe Cys Thr Leu Gly Ala Thr Thr Gly Tyr Leu Lys Gly
        115                 120                 125

Asn Ser Ala Ser Phe Asn Leu Val Gly Leu Phe Gly Thr Lys Thr Gln
    130                 135                 140

Ala Ser Ser Phe Asn Thr Ala Asn Leu Phe Pro Asn Thr Ala Leu Asn
145                 150                 155                 160

Gln Ala Val Val Glu Leu Tyr Thr Asp Thr Thr Phe Ala Trp Ser Val
                165                 170                 175

Gly Ala Arg Ala Ala Leu Trp Glu Cys Gly Cys Ala Thr Leu Gly Ala
            180                 185                 190

Ser Phe Gln Tyr Ala Gln Ser Lys Pro Lys Val Glu Glu Leu Asn Val
        195                 200                 205

Leu Cys Asn Ala Ser Glu Phe Thr Ile Asn Lys Pro Lys Gly Tyr Val
    210                 215                 220

Gly Ala Glu Phe Pro Leu Asp Ile Thr Ala Gly Thr Glu Ala Ala Thr
225                 230                 235                 240

Gly Thr Lys Asp Ala Ser Ile Asp Tyr His Glu Trp Gln Ala Ser Leu
                245                 250                 255

Ala Leu Ser Tyr Arg Leu Asn Met Phe Thr Pro Tyr Ile Gly Val Lys
            260                 265                 270

Trp Ser Arg Val Ser Phe Asp Ala Asp Thr Ile Arg Ile Ala Gln Pro
        275                 280                 285

Lys Leu Ala Glu Ala Ile Leu Asp Val Thr Thr Leu Asn Pro Thr Ile
    290                 295                 300

Ala Gly Lys Gly Thr Val Val Ala Ser Gly Ser Glu Asn Asp Leu Ala
305                 310                 315                 320

Asp Thr Met Gln Ile Val Ser Leu Gln Leu Asn Lys Met Lys Ser Arg
                325                 330                 335

Lys Ser Cys Gly Ile Ala Val Gly Thr Thr Ile Val Asp Ala Asp Lys
            340                 345                 350

Tyr Ala Val Thr Val Glu Thr Arg Leu Ile Asp Glu Arg Ala Ala His
        355                 360                 365

Val Asn Ala Gln Phe Arg Phe
    370                 375

<210> SEQ ID NO 7
<211> LENGTH: 1128
<212> TYPE: DNA
<213> ORGANISM: Chlamydia trachomatis

<400> SEQUENCE: 7
atgcctgtgg ggaatcctgc tgaaccaagc cttatgatcg acggaattct gtgggaaggt      60
ttcggcggag atccttgcga tccttgcacc acttggtgtg acgctatcag catgcgtatg     120
ggttactacg agactttgt tttcgaccgt gttttgaaaa cagatgtgaa taaagaattt     180
cagatgggag cggcgcctac taccaaggat atagcaggct tagaaaacga tccaacaaca     240

```
aatgttgctc gtccaaatcc cgcttatggc aaacacatgc aagatgctga atgtttacg      300
aacgctgctt acatggcatt aaatatctgg gatcgttttg atgtattttg tacattggga      360
gcaactaccg gttatttaaa aggaaactcc gcttccttca acttagttgg attattcgga      420
acaaaaacac aatcttctaa ctttaataca gcgaagctta ttcctaacgc tgctttgaat      480
caagctgtgg ttgagcttta tacagacact acctttgctt ggagcgtagg tgctcgtgca      540
gctctctggg aatgtgggtg tgcaacgtta ggagcttctt ccaatatgc tcaatctaaa       600
cctaaagtag aagagttaaa tgttctttgt aatgcatccg aatttactat taataagccg      660
aaaggatatg ttggggcgga atttccactt gatattaccg caggaacaga agctgcgaca      720
gggactaagg atgcctctat tgactaccat gagtggcaag caagtttagc cctgtcttac      780
agattaaaata tgttcactcc ttacattgga gttaaatggt ctagagtaag ttttgatgcc     840
gacacgatcc gtatcgctca gcctaaattg gctgaagcaa tcttggatgt cactactcta      900
aacccgacca tcgctggtaa aggaactgtg gtcgcttccg gaagcgataa cgacctggct      960
gatacaatgc aaatcgtttc cttgcagttg aacaagatga atctagaaa atcttgcggt      1020
attgcagtag gaacgactat tgtagatgca gacaaatacg cagttacagt tgagactcgc     1080
ttgatcgatg agagagcagc tcacgtaaat gcacaattcc gcttctaa                  1128
```

<210> SEQ ID NO 8
<211> LENGTH: 375
<212> TYPE: PRT
<213> ORGANISM: Chlamydia trachomatis

<400> SEQUENCE: 8

```
Met Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Thr Thr Trp
            20                  25                  30

Cys Asp Ala Ile Ser Met Arg Met Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Ala Pro Thr Thr Lys Asp Ile Ala Gly Leu Glu Asn Asp Pro Thr Thr
65                  70                  75                  80

Asn Val Ala Arg Pro Asn Pro Ala Tyr Gly Lys His Met Gln Asp Ala
                85                  90                  95

Glu Met Phe Thr Asn Ala Ala Tyr Met Ala Leu Asn Ile Trp Asp Arg
            100                 105                 110

Phe Asp Val Phe Cys Thr Leu Gly Ala Thr Thr Gly Tyr Leu Lys Gly
        115                 120                 125

Asn Ser Ala Ser Phe Asn Leu Val Gly Leu Phe Gly Thr Lys Thr Gln
    130                 135                 140

Ser Ser Asn Phe Asn Thr Ala Lys Leu Ile Pro Asn Ala Ala Leu Asn
145                 150                 155                 160

Gln Ala Val Val Glu Leu Tyr Thr Asp Thr Thr Phe Ala Trp Ser Val
                165                 170                 175

Gly Ala Arg Ala Ala Leu Trp Glu Cys Gly Cys Ala Thr Leu Gly Ala
            180                 185                 190

Ser Phe Gln Tyr Ala Gln Ser Lys Pro Lys Val Glu Glu Leu Asn Val
        195                 200                 205
```

Leu Cys Asn Ala Ser Glu Phe Thr Ile Asn Lys Pro Lys Gly Tyr Val
210                 215                 220

Gly Ala Glu Phe Pro Leu Asp Ile Thr Ala Gly Thr Glu Ala Ala Thr
225                 230                 235                 240

Gly Thr Lys Asp Ala Ser Ile Asp Tyr His Glu Trp Gln Ala Ser Leu
                245                 250                 255

Ala Leu Ser Tyr Arg Leu Asn Met Phe Thr Pro Tyr Ile Gly Val Lys
                260                 265                 270

Trp Ser Arg Val Ser Phe Asp Ala Asp Thr Ile Arg Ile Ala Gln Pro
                275                 280                 285

Lys Leu Ala Glu Ala Ile Leu Asp Val Thr Thr Leu Asn Pro Thr Ile
290                 295                 300

Ala Gly Lys Gly Thr Val Val Ala Ser Gly Ser Asp Asn Asp Leu Ala
305                 310                 315                 320

Asp Thr Met Gln Ile Val Ser Leu Gln Leu Asn Lys Met Lys Ser Arg
                325                 330                 335

Lys Ser Cys Gly Ile Ala Val Gly Thr Thr Ile Val Asp Ala Asp Lys
                340                 345                 350

Tyr Ala Val Thr Val Glu Thr Arg Leu Ile Asp Glu Arg Ala Ala His
                355                 360                 365

Val Asn Ala Gln Phe Arg Phe
370                 375

<210> SEQ ID NO 9
<211> LENGTH: 1116
<212> TYPE: DNA
<213> ORGANISM: Chlamydia trachomatis

<400> SEQUENCE: 9
atgcctgtgg ggaatcctgc tgaaccaagc cttatgatcg acggaattct gtgggaaggt      60
ttcggcggag atccttgcga tccttgcgcc acttggtgtg acgctatcag catgcgtgtt     120
ggttactacg gagactttgt tttcgaccgt gttttgaaaa ctgatgtgaa taagaatttt     180
cagatgggtg ccaagcctac aactgataca ggcaatagtg cagctccatc cactcttaca     240
gcaagagaga tcctgcctta cggccgacat atgcaggatg ctgagatgtt acaaatgcc      300
gcttgcatgg cattgaatat ttgggatcgt tttgatgtat tctgtacatt aggagccacc     360
agtggatatc ttaaaggaaa ctctgcttct tcaatttag ttggattgtt tggagataat      420
gaaaatcaaa aaacggtcaa agcggagtct gtaccaaata tgagctttga tcaatctgtt     480
gttgagttgt atacagatac tacttttgcg tggagcgtcg gcgctcgcgc agctttgtgg     540
gaatgtggat gtgcaacttt aggagcttca ttccaatatg ctcaatctaa acctaaagta     600
gaagaattaa acgttctctg caatgcagca gagtttacta ttaataaacc taagggtat      660
gtaggtaagg agtttcctct tgatcttaca gcaggaacag atgctgcgac aggaactaag     720
gatgcctcta ttgattacca tgaatggcaa gcaagtttag ctctctctta cagactgaat     780
atgttcactc cctacattgg agttaaatgg tctcgagcaa gctttgatgc cgatacgatt     840
cgtatagccc agccaaaatc agctacagct atttttgata ctaccacgct taacccaact     900
attgctggag ctggcgatgt gaaaactggc gcagagggtc agctcggaga cacaatgcaa     960
atcgtttcct gcaattgaa caagatgaaa tctagaaaat cttgcggtat tgcagtagga    1020
acaactattg tggatgcaga caaatacgca gttacgttg agactcgctt gatcgatgag     1080
agagcagctc acgtaaatgc acaattccgc ttctaa                              1116

```
<210> SEQ ID NO 10
<211> LENGTH: 371
<212> TYPE: PRT
<213> ORGANISM: Chlamydia trachomatis

<400> SEQUENCE: 10

Met Pro Val Gly Asn Pro Ala Glu Pro Ser Leu Met Ile Asp Gly Ile
1               5                   10                  15

Leu Trp Glu Gly Phe Gly Gly Asp Pro Cys Asp Pro Cys Ala Thr Trp
            20                  25                  30

Cys Asp Ala Ile Ser Met Arg Val Gly Tyr Tyr Gly Asp Phe Val Phe
        35                  40                  45

Asp Arg Val Leu Lys Thr Asp Val Asn Lys Glu Phe Gln Met Gly Ala
    50                  55                  60

Lys Pro Thr Thr Asp Thr Gly Asn Ser Ala Ala Pro Ser Thr Leu Thr
65                  70                  75                  80

Ala Arg Glu Asn Pro Ala Tyr Gly Arg His Met Gln Asp Ala Glu Met
                85                  90                  95

Phe Thr Asn Ala Ala Cys Met Ala Leu Asn Ile Trp Asp Arg Phe Asp
            100                 105                 110

Val Phe Cys Thr Leu Gly Ala Thr Ser Gly Tyr Leu Lys Gly Asn Ser
        115                 120                 125

Ala Ser Phe Asn Leu Val Gly Leu Phe Gly Asp Asn Glu Asn Gln Lys
    130                 135                 140

Thr Val Lys Ala Glu Ser Val Pro Asn Met Ser Phe Asp Gln Ser Val
145                 150                 155                 160

Val Glu Leu Tyr Thr Asp Thr Thr Phe Ala Trp Ser Val Gly Ala Arg
                165                 170                 175

Ala Ala Leu Trp Glu Cys Gly Cys Ala Thr Leu Gly Ala Ser Phe Gln
            180                 185                 190

Tyr Ala Gln Ser Lys Pro Lys Val Glu Glu Leu Asn Val Leu Cys Asn
        195                 200                 205

Ala Ala Glu Phe Thr Ile Asn Lys Pro Lys Gly Tyr Val Gly Lys Glu
    210                 215                 220

Phe Pro Leu Asp Leu Thr Ala Gly Thr Asp Ala Ala Thr Gly Thr Lys
225                 230                 235                 240

Asp Ala Ser Ile Asp Tyr His Glu Trp Gln Ala Ser Leu Ala Leu Ser
                245                 250                 255

Tyr Arg Leu Asn Met Phe Thr Pro Tyr Ile Gly Val Lys Trp Ser Arg
            260                 265                 270

Ala Ser Phe Asp Ala Asp Thr Ile Arg Ile Ala Gln Pro Lys Ser Ala
        275                 280                 285

Thr Ala Ile Phe Asp Thr Thr Thr Leu Asn Pro Thr Ile Ala Gly Ala
    290                 295                 300

Gly Asp Val Lys Thr Gly Ala Glu Gly Gln Leu Gly Asp Thr Met Gln
305                 310                 315                 320

Ile Val Ser Leu Gln Leu Asn Lys Met Lys Ser Arg Lys Ser Cys Gly
                325                 330                 335

Ile Ala Val Gly Thr Thr Ile Val Asp Ala Asp Lys Tyr Ala Val Thr
            340                 345                 350

Val Glu Thr Arg Leu Ile Asp Glu Arg Ala Ala His Val Asn Ala Gln
        355                 360                 365

Phe Arg Phe
    370
```

```
<210> SEQ ID NO 11
<211> LENGTH: 366
<212> TYPE: PRT
<213> ORGANISM: Chlamydia trachomatis

<400> SEQUENCE: 11
```

| | | | | | | | | | | | | | | | |
|---|---|---|---|---|---|---|---|---|---|---|---|---|---|---|---|
| Met | Leu | Pro | Val | Gly | Asn | Pro | Ala | Glu | Pro | Ser | Leu | Met | Ile | Asp | Gly |
| 1 | | | | 5 | | | | | 10 | | | | | 15 | |
| Ile | Leu | Trp | Glu | Gly | Phe | Gly | Gly | Asp | Pro | Cys | Asp | Pro | Cys | Thr | Thr |
| | | | 20 | | | | | 25 | | | | | 30 | | |
| Trp | Cys | Asp | Ala | Ile | Ser | Leu | Arg | Leu | Gly | Tyr | Tyr | Gly | Asp | Phe | Val |
| | | 35 | | | | | 40 | | | | | 45 | | | |
| Phe | Asp | Arg | Val | Leu | Lys | Thr | Asp | Val | Asn | Lys | Gln | Phe | Glu | Met | Gly |
| 50 | | | | | 55 | | | | | 60 | | | | | |
| Ala | Ala | Pro | Thr | Gly | Asp | Ala | Asp | Leu | Thr | Thr | Ala | Pro | Thr | Pro | Ala |
| 65 | | | | 70 | | | | | 75 | | | | | 80 | |
| Ser | Arg | Glu | Asn | Pro | Ala | Tyr | Gly | Lys | His | Met | Gln | Asp | Ala | Glu | Met |
| | | | | 85 | | | | | 90 | | | | | 95 | |
| Phe | Thr | Asn | Ala | Ala | Tyr | Met | Ala | Leu | Asn | Ile | Trp | Asp | Arg | Phe | Asp |
| | | | 100 | | | | | 105 | | | | | 110 | | |
| Val | Phe | Cys | Thr | Leu | Gly | Ala | Thr | Ser | Gly | Tyr | Leu | Lys | Gly | Asn | Ser |
| | | 115 | | | | | 120 | | | | | 125 | | | |
| Ala | Ala | Phe | Asn | Leu | Val | Gly | Leu | Phe | Gly | Arg | Asp | Glu | Thr | Ala | Val |
| 130 | | | | | 135 | | | | | 140 | | | | | |
| Ala | Ala | Asp | Asp | Ile | Pro | Asn | Val | Ser | Leu | Ser | Gln | Ala | Val | Val | Glu |
| 145 | | | | | 150 | | | | | 155 | | | | | 160 |
| Leu | Tyr | Thr | Asp | Thr | Ala | Phe | Ala | Trp | Ser | Val | Gly | Ala | Arg | Ala | Ala |
| | | | | 165 | | | | | 170 | | | | | 175 | |
| Leu | Trp | Glu | Cys | Gly | Cys | Ala | Thr | Leu | Gly | Ala | Ser | Phe | Gln | Tyr | Ala |
| | | | 180 | | | | | 185 | | | | | 190 | | |
| Gln | Ser | Lys | Pro | Lys | Val | Glu | Glu | Leu | Asn | Val | Leu | Cys | Asn | Ala | Ala |
| | | 195 | | | | | 200 | | | | | 205 | | | |
| Glu | Phe | Thr | Ile | Asn | Lys | Pro | Lys | Gly | Tyr | Val | Gly | Gln | Glu | Phe | Pro |
| 210 | | | | | 215 | | | | | 220 | | | | | |
| Leu | Asn | Ile | Lys | Ala | Gly | Thr | Val | Ser | Ala | Thr | Asp | Thr | Lys | Asp | Ala |
| 225 | | | | | 230 | | | | | 235 | | | | | 240 |
| Ser | Ile | Asp | Tyr | His | Glu | Trp | Gln | Ala | Ser | Leu | Ala | Leu | Ser | Tyr | Arg |
| | | | | 245 | | | | | 250 | | | | | 255 | |
| Leu | Asn | Met | Phe | Thr | Pro | Tyr | Ile | Gly | Val | Lys | Trp | Ser | Arg | Ala | Ser |
| | | | 260 | | | | | 265 | | | | | 270 | | |
| Phe | Asp | Ala | Asp | Thr | Ile | Arg | Ile | Ala | Gln | Pro | Lys | Leu | Glu | Thr | Ser |
| | | 275 | | | | | 280 | | | | | 285 | | | |
| Ile | Leu | Lys | Met | Thr | Thr | Trp | Asn | Pro | Thr | Ile | Ser | Gly | Ser | Gly | Ile |
| | | 290 | | | | | 295 | | | | | 300 | | | |
| Asp | Val | Asp | Thr | Lys | Ile | Thr | Asp | Thr | Leu | Gln | Ile | Val | Ser | Leu | Gln |
| 305 | | | | | 310 | | | | | 315 | | | | | 320 |
| Leu | Asn | Lys | Met | Lys | Ser | Arg | Lys | Ser | Cys | Gly | Leu | Ala | Ile | Gly | Thr |
| | | | | 325 | | | | | 330 | | | | | 335 | |
| Thr | Ile | Val | Asp | Ala | Asp | Lys | Tyr | Ala | Val | Thr | Val | Glu | Thr | Arg | Leu |
| | | | 340 | | | | | 345 | | | | | 350 | | |
| Ile | Asp | Glu | Arg | Ala | Ala | His | Val | Asn | Ala | Gln | Phe | Arg | Phe | | |
| | | 355 | | | | | 360 | | | | | 365 | | | |

IMMUNOGENIC COMPOSITIONS

CROSS-REFERENCE TO RELATED APPLICATIONS

The present application is a 35 U.S.C. §371 national stage application of International Application No. PCT/CA2011/050705, filed Nov. 15, 2011, and claims priority to U.S. provisional application 61/413,699 filed Nov. 15, 2010, which are incorporated by reference herein in their entirety.

BACKGROUND

This invention relates to the field of immunogenic compositions which comprise an adjuvant. More particularly, the invention relates to adjuvanted immunogenic compositions (e.g., vaccines) against at least one or more *Chlamydia* species.

Chlamydial bacteria are obligate intracellular pathogens of eukaryotic cells. Three species of the family *Chlamydia* infect humans—*C. trachomatis, C. pneumoniae*, and *C. psittaci*—and genomic sequences for each of these are publicly available.

*C. trachomatis* organisms are dimorphic, and alternate between two distinct morphological forms, the infectious elementary bodies (EB) and the metabolically active reticulate bodies (RB). The EBs infect eukaryotic cells; they are endocytosed by mucosal cells into vesicular inclusions and are transformed into RB. Within the inclusion, the RBs replicate and redifferentiate into EBs before being released through cell lysis to infect neighbouring cells.

*Chlamydia trachomatis* is the most prevalent sexually transmitted bacterial pathogen in the world, with an estimated 100 million clinically diagnosed cases occurring annually. In addition, a similar or greater number of asymptomatic cases go undetected. The most common clinical presentations are urethritis and cervicitis. These acute manifestations typically resolve over a period of a few weeks. However, in certain patients, long-term sequelae may develop, including pelvic inflammatory disease, ectopic pregnancy, and infertility. In areas of the world with poor hygienic conditions, *Chlamydia trachomatis* causes trachoma and lymphogranuloma venerum (LGV). Although effective antibiotic therapy is available, eradication of these organisms will most likely only be achieved through a vaccination program. To date, no vaccine is commercially available against this infection.

Compositions including the major outer membrane protein (referenced herein as "MOMP") of *Chlamydia trachomatis* are known. In particular, the article entitled, "Vaccination with the *Chlamydia trachomatis* Major Outer Membrane Protein Can Elicit an Immune Response as Protective as That Resulting from Inoculation with Live Bacteria", Sukumar Pal et. al., Infection and Immunity, December 2005, p. 8153-8160 discloses the use of *Chlamydia* antigens in conjunction with adjuvants in an immunization composition. The publication discloses studies using the adjuvants CpG+alum, or CpG+Montanide ISA 720. According to the authors of this publication, the results obtained with these adjuvants were quite encouraging, but still required improvement. Moreover, while these adjuvants are quite suitable for animals, their ability to be used in humans is uncertain. Indeed, CpG oligonucleotides have been known to perform well in animals, but not so well in humans and Montanide ISA 720, a water-in-oil emulsion, can be rather painful when administered to humans.

Therefore, there still remains a need for a safe and effective immunogenic composition against Chlamydial infections.

SUMMARY OF THE INVENTION

The present invention provides compositions such as immunogenic compositions (e.g., vaccine compositions), comprising a Chlamydial major outer membrane protein (referenced herein as "MOMP") from at least one Chlamydial serovar, and an adjuvant, characterized in that the adjuvant comprises at least the product E6020 having CAS Registry Number 287180-63-6. In these embodiments, the adjuvant may further comprise at least one carrier system (such as e.g., emulsion, mineral particle).

The MOMP protein may be derived from any species of *Chlamydia* (e.g., *C. trachomatis, C. pneumoniae, C. psittaci*, or *C. trachomatis* MoPn). In preferred embodiments, the composition comprises one or more major outer membrane proteins each derived from different serovars of *C. trachomatis*. The invention also provides methods of inducing an immune response to a *Chlamydia* species (e.g., *C. trachomatis*) in a subject, by administering to the subject a composition of the invention.

In one example the Chlamydial major outer membrane protein is derived from any species of *Chlamydia* (e.g. *C. trachomatis, C. pneumoniae, C. psittaci*, or *C. trachomatis* mouse pneumonitis (MoPn)). In preferred embodiments, the major outer membrane protein is derived from *C. trachomatis*. In a preferred embodiment, the composition includes two, three, four or more (e.g., five) Chlamydial major membrane proteins each derived from a different serovar of *C. trachomatis*.

According to an embodiment of the present invention, the composition also comprises a carrier system which may assist in the delivery of the antigen and/or the product E6020, or which may increase the adjuvant effect of E6020.

This carrier system can comprise a suspension of aluminum salts, such as aluminum hydroxide, aluminum phosphate, aluminum hydroxyphosphate, or a mixture of them. In preferred embodiments, aluminum hydroxide is included.

According to an embodiment, the carrier may comprise an emulsion, and particularly an oil-in-water emulsion.

According to a further embodiment of the present invention, the composition also comprises an immunostimulant such as a Toll-like Receptor 7/8 agonist, and particularly an imidazoquinoline product.

The compositions can be in liquid form, dry powder form, freeze dried, spray dried or foam dried.

Specific examples of the compositions of the invention include those set out in the examples herein such as for example, the Adjuvants of the invention, ADJ.A, and ADJ.B.

The invention also provides a method of making compositions comprising at least one recombinant Chlamydial MOMP, and an adjuvant, characterized in that the adjuvant comprises at least product E6020 having CAS Number 287180-63-6.

The method includes providing at least one Chlamydial MOMP and admixing the at least one recombinant MOMP with an adjuvant, the adjuvant comprising at least product E6020 having CAS Number 287180-63-6.

The invention also provides methods of inducing an immune response to a *Chlamydia* species (e.g., *C. trachomatis*) in a subject, which involve administering to the subject a composition as described herein. In addition, the invention includes use of the compositions of the invention in inducing an immune response to *Chlamydia* species (e.g., *C. trachomatis*).

The invention provides a number of advantages. For example, in addition to being safe for human use, the immunogenic composition of the present invention provides an immune response which is both significant and Th1 oriented or Th1/Th2 balanced and therefore, favorable for a *Chlamydia* vaccine. Other features and advantages of the invention will be apparent from the following Detailed Description, the Drawings, and the Claims.

BRIEF DESCRIPTION OF THE DRAWINGS

FIG. 1: shows a representative Blue Native PAGE gel analysis of rMOMP (serovar E, *C. trachomatis*) protein samples: two pilot scale samples (left, A,B) and three lab scale samples (right, C-H)

FIG. 2: shows a representative SDS-PAGE gel of rMOMP (serovar E, *C. trachomatis*) pilot scale (JR3182) protein samples demonstrating the structure of the rMOMP protein at various steps (i.e., samples of the solubilized IBs, the purified denatured MOMP (Q pool), the folded protein, and the final product)

DETAILED DESCRIPTION

The present invention provides immunogenic compositions (e.g., vaccine compositions), comprising a Chlamydial MOMP from at least one Chlamydial serovar and an adjuvant, characterized in that the adjuvant comprises at least the product E6020 having CAS Number 287180-63-6.

The Chlamydial MOMP that can be included in the compositions of the invention can be derived from any species of *Chlamydia* (such as for example, *C. trachomatis, C. pneumoniae, C. psittaci, C. pecorum* or *C. trachomatis* MoPn).

MOMP constitutes 60% of the mass of the outer membrane and is surface exposed. The MOMP that can be included in the compositions of the invention can be extracted from natural EB, or can be produced recombinantly using any of a number of methods known in the art. In light of the difficulties of producing sufficient quantities in a purified form, recombinant MOMPs are preferable for the present invention. Such recombinantly derived antigens, are often less immunogenic than their native counterparts (in part due to their high level of purity), and as such may need to be administered with an adjuvant particularly one that elicits a robust (or potent) immune response (as opposed to a weak one).

Preferably the recombinant MOMP is in a purified, refolded and soluble form. For example, the recombinant protein can be prepared in accordance to the methods described in co-pending PCT Application (claiming priority to U.S. Ser. Nos. 61/413,663 and 61/452,319). In one example, a recombinant Chlamydial MOMP, that is expressed as an insoluble aggregate in a heterologous host, is obtained in a soluble and immunogenic form in accordance to a method comprising the steps of:

(a) isolating said insoluble aggregated protein;

(b) admixing said insoluble aggregated protein from step (a) in an aqueous solution comprising a denaturing agent to denature said insoluble aggregated protein;

(c) purifying the denatured protein from step (b) by subjecting the mixture of step (b) to at least one chromatographic purification in the presence of denaturing agent and collecting eluted solution of purified denatured protein;

(e) admixing the purified denatured protein solution from step (c) with a reducing agent and at least one small molecule additive; and (f) reducing concentration of denaturing agent and reducing agent to levels sufficient to allow the protein to renature into soluble and substantially oligomeric forms.

In preferred embodiments, the composition comprises at least one MOMP from *Chlamydia trachomatis. Chlamydia trachomatis* includes multiple serovars. The MOMPs encoded by different *C. trachomatis* serovars share five well-conserved regions and four variable sequence segments or domains (termed VS or VD 1 to VD 4) which contain subspecies and serovar specific antigenic determinants (Baehr et al., 1988; Yuan et al., 1989]. There are at least 19 different *C. trachomatis* serovars capable of infecting humans (i.e., A to K, Ba, Da, Ia, Ja, L1, L2, L3 and L2a).

Serovars have been typed based on serological differentiation of the antigenic epitopes on MOMP and, based on amino acid homology, have been placed into the following serogroups or classes: B class (B, Ba, D, Da, E, L1, L2 and L2a), C class (A, C, H, I, Ia, J, K and L3), and intermediate class (F and G) (Schachter, J., and C. Dawson. 1978. Human chlamydial infections. PSG Publishing Company, Inc., Littleton, Mass.). Infection with any *C. trachomatis* serovar may result in disease: serovars A, B, Ba and C cause trachoma; the LGV serovars L1, L2 and L3 cause lymphogranuloma venereum; and serovars D-K cause genital, respiratory and ocular infections; and serovars G, I and D have been associated with cervical cancer.

In preferred embodiments, the compositions of the invention include MOMP from two or more of the *C. trachomatis* serovars, to protect against a wider range of serovars. Preferably, the chosen serovars are those which are necessary to protect against the most pathogenic (or most prevalent) serovars which are circulating in the world (e.g. serovars E, D and F). In one example, the composition includes three MOMPs, one from each of serovars E, D and F. In a separate example, the composition includes five MOMPs, one from each of serovars E, D, F, J and I.

The antigens are administered at a dose sufficient to raise an immune response; preferred administration doses include 50 μg of antigen/dose, 1-250 μg/dose, 10-100 μg/dose, 25-75 μg/dose or 5-25 μg/dose. The antigens (e.g., recombinantly-derived) are administered with an adjuvant to increase immunogenicity.

According to the present invention, the adjuvant comprises at least the product E6020 having CAS Registry Number 287180-63-6. Such a product is described in patent application US2007/0082875 and has the following chemical formula:

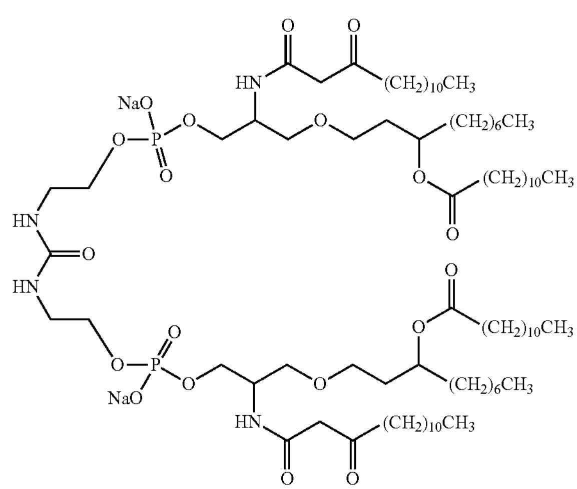

This product contains asymmetric carbon atoms and hence can exist as stereoisomers. One preferable stereoisomer for the composition of the present invention is the one in which all the asymmetric carbons are R, which gives the following structure:

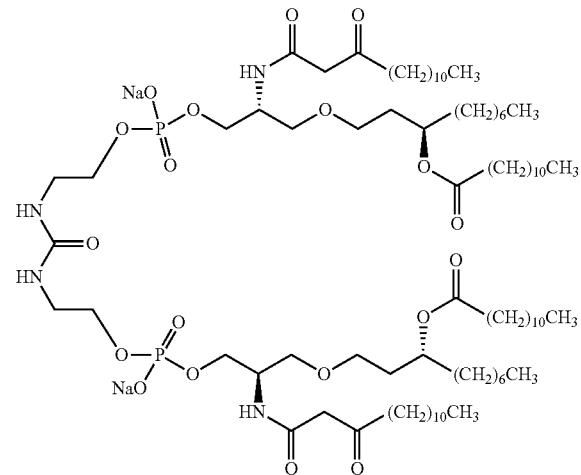

According to a preferred embodiment, the composition according to the present invention also comprises a carrier system, such as e.g. emulsions, mineral particles, lipid particles, polymer particles, and protein particles (antigen-based particles i.e. VLPs and the like). Among these, preferred carrier systems are mineral particles or emulsions.

Preferred mineral particles include suspensions of mineral salts, such as for example, suspensions of iron salts, calcium salts, or aluminum salts. In vaccine compositions, aluminum salts are a commonly used mineral salt.

The aluminum-based adjuvants which are suitable for use are those which are commonly referred to as aluminum phosphates, which includes those that are from a chemical point of view constituted exclusively of aluminum phosphate and those which also include other salts (e.g., aluminum hydroxide), Examples include, the aluminum phosphate, Adjufos® (supplied by Brenntag Biosector a/s) and the aluminum phosphate, Rehydraphos®, (supplied by Reheis). Other examples include aluminum complexes obtained by the reaction of sodium carbonate in PBS buffer with aluminum potassium sulfates. Aluminum-based adjuvants suitable for use also include aluminium complexes known in the vaccine adjuvant field as aluminum hydroxides, which from a chemical point of view, includes those that are not constituted exclusively of aluminum hydroxide, and those which are oxyhydroxides. Examples include, Alhydrogel® (supplied by Brenntag Biosector a/s) and Rehydragel® (supplied by Reheis). A description of the aluminum salts suitable for use in the invention is set out in WO2007/052058 (pages 9-10) (equivalent of U.S. application Ser. No. 12/092,163 filed Nov. 6, 2006 as US 2009/0304739 A1), which is incorporated herein.

The amount of aluminum is advantageously chosen so as to have less than 1.25 mg of $Al^{3+}$ as recommended by Health Authorities. This amount is preferably between 300 and 600 µg/dose, when the dose is an adult one, and could be less in the case of paediatric dose.

For compositions according to the present invention comprising aluminum salts, the E6020 product may be adsorbed to the aluminum particles before the one or more MOMP antigens are adsorbed to the aluminum particles or it may be mixed following antigen adsorption with the resulting MOMP/aluminum particle.

Specific examples of the compositions of the invention include those set out in the examples herein such as for example, the Adjuvant of the invention, ADJ.B which comprises E6020 and an aluminum carrier system.

The composition of the present invention can also have as a carrier system, an emulsion, which according to a preferred embodiment can be an oil-in-water emulsion.

Various convenient emulsions are known, and they typically include at least one oil and at least one surfactant. The oil droplets in the emulsion are preferably with a size less than 220 nm as they can be submitted to filter sterilization. Preferred emulsions have the majority of their oil droplets which are less than 150 nm and even less than 100 nm.

The invention can be used with oils such as those from an animal (such as fish), vegetable or yeast source. Among the convenient oils, squalene coming from different origins has been successfully used. Other preferred oils are the tocopherols. Mixtures of oils can also be used. For a review of the different emulsions which can possibly be used in the vaccine field, reference can be made to WO2007/052155. Preferred emulsions according to the present invention are those comprising squalene, Tween™ 80, and Span™ 85, such as for example, MF59, or those comprising squalene, a tocopherol, and Tween™ 80. Emulsions which have given particularly good results are emulsions comprising: squalene; a non-ionic hydrophilic surfactant; and a non-ionic hydrophobic surfactant. Such emulsions have been described in US Patent Application No. 2007-0014805-A1 which is incorporated herein.

Squalene is an oil that initially was derived from shark liver. A plant derived squalene (e.g., extracted from olive oil) also exists. Squalene's empirical chemical formula is $C_{30}H_{50}$, comprising 6 double bonds. The oil is metabolizable and has qualities that allow it to be used in an injectable pharmaceutical product. Particularly good results have been obtained using the squalene provided by Fluka (Sigma-Aldrich) which is of animal origin.

The amounts of squalene used for the preparation of a concentrated emulsion are advantageously between 5 and 45%; this concentrated emulsion is subsequently diluted during the preparation of the immunogenic compositions so as to prepare immunizing doses in which the amount of squalene is between 0.5 and 5%, and particularly 1 or 2.5%.

In accordance to the invention, the emulsion comprises a non-ionic hydrophilic surfactant, with a hydrophilic/lipophilic balance, or HLB, the value of which is greater than or equal to 10, and which belongs to the chemical group of polyoxyethylene alkyl ethers (PAEs), also called polyoxyethylenated fatty alcohol ethers, or n-alcohol polyoxyethylene glycol ethers, or macrogol ethers. These nonionic surfactants are obtained by chemical condensation of a fatty alcohol and ethylene oxide. They have a general chemical formula $CH_3(CH_2)_x—(O—CH_2—CH_2)n-OH$, in which "n" denotes the number of ethylene oxide units (typically 10-60), and (x+1) is the number of carbon atoms in the alkyl chain, typically 12 (lauryl(dodecyl)), 14 (myristyl(tetradecyl)), 16 (cetyl(hexadecyl)), or 18 (stearyl(octadecyl)), so "x" is in the range of from 11 to 17. Polyoxyethylene alkyl ethers tend to be mixtures of polymers of slightly varying molecular weights. Accordingly, the emulsions of the invention may comprise a mixture of polyoxyethylene ethers and as such, references made herein to a particular polyoxyethylene ether for use in an emulsion, the recited ether is the primary but not necessarily the only polyoxyethylene alkyl ether present in the emulsion.

The emulsion of the carrier system of the present invention usually comprises a single hydrophilic PAE. A mixture of several PAEs is also suitable insofar as the overall HLB value is ≥10.

The polyoxyethylenated fatty alcohol ethers suitable for use can be, at ambient temperature, in liquid or solid form. Preferential solid compounds are those which dissolve directly in the aqueous phase or which do not require substantial heating.

Insofar as the number of ethylene oxide units is sufficient, polyoxyethylenated ethers of lauryl alcohol, myristyl alcohol, cetyl alcohol, oleyl alcohol and/or stearyl alcohol are particularly suitable for the subject of the invention. Some of them can be found among products known under the trade names Brij® for the products sold by the company ICI America's Inc., Eumulgin® for the products sold by the company Cognis, or Simulsol® for the products sold by the company Seppic.

An emulsion which may be used as a carrier system in the present invention contains, as hydrophilic nonionic surfactant, a polyoxyethylene alkyl ether chosen from the group consisting of ceteareth-12 (sold under the name Eumulgin® B1), ceteareth-20 (Eumulgin®. B2), steareth-21 (Eumulgin® S21), ceteth-20 (Simulsol® 58 or Brij® (58), ceteth-10 (Brij® 56), steareth-10 (Brij® 76), steareth-20 (Brij®78), oleth-10 (Brij® 96 or Brij®97) and oleth-20 (Brij®98 or Brij®99), where the number attributed to each chemical name corresponds to the number of ethylene oxide units in the chemical formula.

Good results have been obtained with the product Brij® 56. A compound that is particularly suitable and preferred because of its semi-synthetic origin is polyoxyethylene (12) cetostearyl ether, provided by the company Cognis under the name Eumulgin®B1. This product is a mixture consisting essentially of $CH_3(CH_2)_{15}$—(O—$CH_2$—$CH_2$)$_{5-23}$—OH and $CH_3(CH_2)_{17}$—(O—$CH_2$—$CH_2$)$_{5-23}$—OH, but with also some $CH_3\ (CH_2)_{16}$—(O—$CH_2$—$CH_2$)$_{5-23}$—OH and some $CH_3(CH_2)_{19}$—(O—$CH_2$—$CH_2$)$_{5-23}$—OH.

The emulsion of the carrier system of the present invention also comprises a hydrophobic nonionic surfactant which is pharmaceutically acceptable. Surfactants that are suitable in this regard, include for example, sorbitan ester or mannide ester surfactants. Sorbitan ester surfactants are obtained by reaction of a fatty acid and of a mixture of partial esters of sorbitol and its mono- and dianhydrides; this may involve a mono-, a di- or a triester, or even a mixture. They are hydrophobic surfactants for which the overall hydrophilic-lipophilic balance (HLB) is less than 9, and preferably less than 6. Some examples can be found among the surfactants sold by the company ICI Americas Inc. under the name Span®, or by the company Cognis under the name Dehymuls™, or by the company ICI under the name Arlacel™. Examples of surfactants that are particularly suitable, include the sorbitan oleate sold under the name Dehymuls SMO™ or Span®80 or Montane™80. Useful mannide ester surfactants include the mannide monooleate (for example, as sold by the company Sigma, or by the company Seppic under the name Montanide 80™). Notably, these products are typically less than 100% pure, and depending upon their origin, in addition to oleates (mono, di and tri-oleates), they can also contain other esters such as palmitates or linoleates.

According to the present invention, this emulsion is prepared through a PIT (i.e., Phase Inversion Temperature) process which leads to a monodisperse emulsion, the droplet size of which is very small, which makes the emulsion very stable. This process comprises a step in which a water-in-oil inverse emulsion is obtained by raising the temperature and a step in which the water-in-oil inverse emulsion is converted to an oil-in-water emulsion by lowering the temperature. This conversion takes place when the water-in-oil emulsion obtained is cooled to a temperature below the phase inversion temperature of this emulsion.

Specific examples of the compositions of the invention include those set out in the examples herein such as for example, the Adjuvant of the invention, ADJ.A which comprises E6020 and an emulsion carrier system.

The compositions of the invention further comprise an aqueous solvent, such as, for example, water or saline, and may also be buffered, such as with a phosphate or a citrate buffer.

The present invention is also related to a method of making the described compositions. According to one embodiment, the method comprises a mixture of at least one antigen with the product E6020.

According to a preferred embodiment, the method includes the preparation of a carrier system comprising a water-in-oil emulsion which includes E6020. This can for example be obtained by carrying out a first step in which an aqueous phase comprising an aqueous solvent, a polyoxyethylene alkyl ether and E6020 is mixed with an oily phase comprising squalene and a nonionic hydrophobic surfactant so as to obtain a coarse oil-in-water emulsion, and a second step in which the oil-in-water emulsion is heated to a temperature which is at least the phase inversion temperature of the emulsion.

According to the method of preparing the carrier system, the aqueous phase comprising the aqueous solution (usually a buffered solution), the E6020 and the nonionic hydrophilic surfactant is incorporated into the oily phase comprising the squalene, and the nonionic hydrophobic surfactant, or vice versa. This incorporation is carried out with mechanical stirring. A noncalibrated, unstable coarse oil-in-water emulsion is thus obtained (preemulsion). This preemulsion is heated under mechanical stirring until phase inversion is obtained (i.e. a water-in-oil emulsion is obtained). The phase inversion or transition can be followed by conductimetry. The temperature at which the curvature change reflecting the passage from one type of emulsion to another occurs is called the phase inversion temperature. In reality, this temperature is a temperature range rather than a very specific point value; in fact, it may be considered that this temperature is capable of varying by one or two degrees, so that the entire emulsion undergoes the phase inversion phenomenon.

When the emulsion is in the form of a water-in-oil emulsion, an abrupt drop in the conductivity is observed. The heating is stopped and the mixture is cooled. The cooling can be carried out passively, by simply allowing the temperature to return spontaneously to ambient temperature, or more actively, by, for example, immersing the emulsion in an ice bath.

As the temperature decreases, the water-in-oil emulsion will again inverse at the phase inversion temperature so as to again give an oil-in-water emulsion. This emulsion is a monodisperse emulsion, where the majority of the oil droplets are less than 150 nm, and even more preferably around 100 nm. Such emulsion has been shown to be very stable over time. It can be stored in this form (monodisperse) and later diluted with a solution comprising the vaccine antigen. This monodisperse emulsion is thermo reversible, which means that, if it is again brought to a temperature at least equal to the phase inversion temperature, it will again become a water-in-oil emulsion. The phase inversion temperature is usually between 45 and 80° C., and typically between 50 and 65° C. In cases where the oil droplets are not of the desired size, the process steps of $1^{st}$ heating and then cooling can be repeated several times until the right size is obtained.

With this method, the components of the composition, in particular E6020, are thus subjected to moderate heating which prevents evaporation of the aqueous phase or chemical degradation of the components.

In an alternative embodiment, the water-in-oil emulsion is obtained by separately heating the aqueous and the oily phases at a temperature which is at least equal to the phase inversion temperature of the emulsion, and by then mixing both phases keeping the temperature of the mixture at a temperature which is at least equal to the phase inversion temperature. The water-in-oil emulsion is subsequently cooled so that a submicronic oil-in-water emulsion is obtained.

Alternatively, E6020 can be introduced into the oily phase instead of being introduced into the aqueous phase. Or, in another interesting alternative embodiment, the oil-in-water emulsion is first prepared, and E6020 is then added to the prepared emulsion.

In other embodiments, E6020 is introduced after mixing the oily and the aqueous phases, or after the emulsion has already been heated and is in a water-in-oil emulsion form.

The aqueous phase may also contain an alditol.

In the adjuvant according to the present invention, E6020 is present in an amount that is both sufficient to stimulate the immune system and safe for administration to subjects (e.g., humans). Accordingly, the quantity of E6020 is preferably less than 40 µg/ml, preferably 20 µg/ml, 15 µg/ml, 10 µg/ml, 5 µg/ml, 4 µg/ml in the administered immunization composition.

The efficacy of the compositions of the present invention has been evaluated in animal models. Such studies have been recognized in the field as a convenient way to predict efficacy in human subjects. As described in the exemplifications provided herein, immunogenicity studies were performed in mice to assess a number of criteria:

MOMP-specific antibody responses,
in vitro neutralizing activity of antisera,
type 1 cellular immune responses as indicated by elevated IFN-γ and decreased IL-4 production,
type 2 cellular immune responses as indicated by measuring IL-4, IL-5 and IL-10 production.

Challenge tests on mice were also performed to test the protective efficacy of the immunization compositions. These tests were performed according to an intravaginal challenge model and an intrabursal challenge murine infertility model.

The present invention provides immunogenic compositions useful for treating and/or preventing Chlamydial infections. In another aspect, the present invention provides methods of inducing anti-chlamydial immunity by administering the immunogenic compositions provided, either alone or in a prime boost protocol. An anti-chlamydial immune response can be defined as a reduction in bacterial load in the immunized host upon challenge with live *Chlamydia*, and/or the stimulation of protective levels of IFN-γ in the host cells (immunoprotective response).

In certain embodiments, the immunogenic composition includes at least one *Chlamydia* outer membrane protein made in accordance to the methods described herein. For example, the immunogenic composition may include MOMP from at least one serovar of a *Chlamydia* species (e.g., *C. trachomatis*) and preferably, it includes MOMP from at least two or at least three or more serovars of a *Chlamydia* species. Preferably, the immunogenic composition prevents infection in a subject by inducing functional antibodies and appropriate CD4 and CD8 T-cell responses. Ideally, the composition elicits its appropriate functional antibodies and IFN-γ producing CD4 T-cells (analogous to a Th1 type response in mice).

The immunogenic compositions of the present invention are preferably in liquid form, but they may be lyophilized (as per standard methods) or foam dried (as described in WO2009012601, Antigen-Adjuvant Compositions and Methods). A composition according to one embodiment of the invention is in a liquid form. An immunization dose may be formulated in a volume of between 0.5 and 1.0 ml. Liquid formulations may be in any form suitable for administration including for example, a solution, or suspension.

The pH of the formulation (and composition) is preferably between about 6.4 and about 9. More preferably, the pH is about 7.4. The pH may be maintained by the use of a buffer.

The pharmaceutical formulations of the immunogenic compositions of the present invention may also optionally include one or more excipients (e.g., diluents, buffers, preservatives, detergents and/or immunostimulants) which are well known in the art. Suitable excipients are compatible with the antigen and with the adjuvant as is known in the art. Examples of detergents include a Tween (polysorbate) such as Tween 80.

The immunogenic compositions of the invention find use in methods of preventing or treating a disease, disorder condition or symptoms associated with *Chlamydia*. The terms disease disorder and condition will be used interchangeably herein. Specifically the prophylactic and therapeutic methods comprise administration of a therapeutically effective amount of a pharmaceutical composition to a subject. In particular embodiments, methods for preventing or treating *Chlamydia* are provided.

As used herein, preventing a disease or disorder is intended to mean administration of a therapeutically effective amount of a pharmaceutical composition of the invention to a subject in order to protect the subject from the development of the particular disease or disorder associated with *Chlamydia*.

By treating a disease or disorder is intended administration of a therapeutically effective amount of a pharmaceutical composition of the invention to a subject that is afflicted with a disease caused by *Chlamydia* or that has been exposed to *Chlamydia* where the purpose is to cure, heal alleviate relive alter remedy ameliorate improve or affect the condition or the symptoms of the disease.

A therapeutically effective amount refers to an amount that provides a therapeutic effect for a given condition and administration regimen. A therapeutically effective amount can be determined by the ordinary skilled medical worker based on patient characteristics (e.g., age, weight, gender, condition, complications other diseases). The therapeutically effective amount will be further influenced by the route of administration of the composition.

For prophylactic uses, one skilled in the art can readily determine the appropriate dose, frequency of dosing and route of administration. Factors in making such determinations include, without limitation, the nature of the protein to be administered, the condition to be treated, potential patient compliance, the age and weight of the patient and the like. The immunogenic preparations and vaccines are administered in a manner compatible with the dosage formulation, and in such amount as will be therapeutically effective (i.e., protective against Chlamydial infection). The quantity to be administered is subject dependent, including for example the capacity of the individual's immune system to synthesize antibodies to the composition and produce a cell-mediated immune response. Suitable dosage ranges are readily determinable by one skilled in the art and may be of the order of about 1 µg to about 1 mg of the soluble, immunogenic recombinant protein (e.g., rMOMP). Suitable regimes for initial administration and booster doses are also variable but may include an initial administration followed by subsequent administration. The dosage may also depend on the route of administration and will vary according to the size of the subject. The invention also provides compositions including antigenic material of several pathogens (combined vaccines). Such combined vaccines contain for example material from various pathogens or from various strains of the same pathogen, or from combinations of various pathogens.

Immunogenic compositions may be presented in a kit form comprising the immunogenic composition and an adjuvant or a reconstitution solution comprising one or more pharmaceutically acceptable diluents to facilitate reconstitution of the composition for administration to a mammal using conventional or other devices. Such a kit would optionally include the device for administration of the liquid form of the composition (e.g. hypodermic syringe, microneedle array) and/or instructions for use.

The present disclosure also provides methods of eliciting an immune response in a subject by administering the immunogenic compositions, or formulations thereof, to subjects. This may be achieved by the administration of a pharmaceutically acceptable formulation of the compositions to the subject to effect exposure of the immunogenic polypeptide and/or adjuvant to the immune system of the subject. The administrations may occur once or may occur multiple times. In one example, the one or more administrations may occur as part of a so-called "prime-boost" protocol.

Compositions of the invention can be administered by an appropriate route such as for example, percutaneous (e.g., intramuscular, intravenous, intraperitoneal or subcutaneous), transdermal, or mucosal (e.g., intranasal), in amounts and in regimes determined to be appropriate by those skilled in the art. Exposure of the subject to the compositions disclosed herein may result in establishment of a temporary or permanent immune response in the subject. The immune response may protect the subject from subsequent exposure to the antigen, often by subsequent exposure to an infectious agent from which the antigen was derived. Therapeutic effects may also be possible.

The composition may be administered in dosage unit formulations containing conventional pharmaceutically acceptable carriers and vehicles. The term "pharmaceutically acceptable carrier" as used herein refers to one or more formulation materials suitable for accomplishing or enhancing the delivery of a protein or polypeptide as a pharmaceutical composition. In certain embodiments, a pharmaceutical composition is a composition comprising a therapeutically effective amount of a polypeptide or protein. The terms "effective amount" and "therapeutically effective amount" each refer to the amount of a polypeptide or protein used to induce or enhance an effective immune response. It is preferred that compositions of the present invention provide for the induction or enhancement of an immune response in a host which protects the host from the development of an infection or allows the host to eliminate an existing infection from the body.

The compositions and vaccines disclosed herein may also be incorporated into various delivery systems. In one example, the compositions may be applied to a "microneedle array" or "microneedle patch" delivery system for administration. These microneedle arrays or patches generally comprise a plurality of needle-like projections attached to a backing material and coated with a dried form of a vaccine. When applied to the skin of a subject, the needle-like projections pierce the skin and achieve delivery of the vaccine, effecting immunization of the subject.

While the compositions of the invention can be administered as the sole active pharmaceutical agent, they can also be used in combination with one or more other compositions or agents (i.e., other chlamydial antigens, co-stimulatory molecules, adjuvants). When administered as a combination, the individual components can be formulated as separate compositions administered at the same time or different times, or the components can be combined as a single composition.

As used herein, the term "subject", is meant any mammalian subject, particularly humans. Other subjects may include cattle, sheep (e.g. in detection of sheep at risk of abortion due to chlamydial infection), dogs, cats (e.g. in detection of cats having eye and/or respiratory infections), pigs, horses, and so on. Of particular interest are subjects having or susceptible to *Chlamydia* infection, particularly to infection by *C. trachomatis, C. psittaci* and/or *C. pneumoniae*.

All references cited within this disclosure are hereby incorporated by reference in their entirety.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

Preparation of the MOMP Antigen

To mimic the human infection process, MOMP was isolated from the *C. trachomatis* mouse pneumonitis strain (MoPn), a natural murine pathogen that was originally recovered from mice inoculated with human respiratory tract specimens. Inoculation of the genital tract of female mice with MoPn results in an infection that parallels that experienced in humans, resulting in, for example, vaginal shedding for several weeks and the development of infertility.

The *C. trachomatis* MoPn biovar (strain Nigg II) was purchased from the American Type Culture Collection (Manassas, Va.) and grown in HeLa 229 cells. The elementary bodies (EB) were prepared as described by Caldwell et al. (Caldwell, H. D., J. Kromhout, and J. Schachter. 1981. Purification and characterization of the major outer membrane protein of *Chlamydia trachomatis*. Infect. Immun. 31:1161-1176). The organisms were frozen at −70° C. in SPG (0.2 M sucrose, 20 mM sodium phosphate [pH 7.4], and 5 mM glutamic acid).

*C. trachomatis* MoPn grown in HeLa 229 cells was washed with 10 mM phosphate-buffered saline (PBS), pH 7.4, and centrifuged and the pellet was treated with DNase. Following centrifugation, the pellet was resuspended in 0.2 M phosphate buffer, pH 5.5, containing 0.001 M concentrations (each) of EDTA and phenylmethylsulfonyl fluoride (PMSF) and was extracted with 3-[(3-cholamidopropyl)-dimethylammonio]-1-propane sulfonate (CHAPS; Calbiochem-Novabiochem Corp., San Diego, Calif.) and Zwittergent 3-14 (Z3-14; Calbiochem-Novabiochem Corp.). The MOMP was recovered in the supernatant and purified using a 1-cm by 35-cm hydroxylapatite column. Fractions containing the MOMP were pooled, run on a 5 to 20% gradient sodium dodecyl sulfate-polyacrylamide gel electrophoresis (SDS-PAGE), and stained with silver and Coomassie blue (Bio-Rad, Hercules, Calif.). In addition, an N-terminal amino acid analysis was performed on the purified MOMP by the core facilities at the University of California, Irvine.

The MOMP was refolded by dialysis against 0.1M phosphate buffer, pH 7.8, containing 0.001M EDTA, 0.002 M reduced glutathione, 0.001M oxidized glutathione, and 0.05% Z3-14 at room temperature at a protein concentration of 30 to 150 µg/ml. The MOMP was concentrated and fixed with 20% glutaraldehyde (for a final concentration of 2% glutaraldehyde) for 2 min at room temperature, and subsequently 2 M glycine was added (for a final concentration of 0.2M glycine) to stop the reaction. Before fixation and inoculation, the protein preparation was concentrated using PEG-20,000 or Centricon-10 filters and dialyzed against a solution containing 0.02 M phosphate buffer, pH 7.4, 0.15 M NaCl, and 0.05% Z3-14.

Example 2

Murine Test in a Low Dose Challenge Model

Immunization compositions according to the present invention were evaluated in a low dose challenge model to assess their ability to protect against overt genital infection.

The composition according to the present invention was prepared as follows:
(i) MOMP antigen was prepared from MoPn substantially as described in Example 1;
(ii) The adjuvant of the invention (ADJ.A) was prepared as follows:

In a $1^{st}$ container, the following ingredients were mixed, under agitation and at 40° C.:
39.37 g of Phosphate Buffer, (Eurobio)
4.68 g of mannitol, (Roquette)
4.822 g of Eumulgin™ B1, (Cognis)
and 20.3 mg of E6020 (Eisai).
This aqueous phase had a weight of 48.91 g.

In a $2^{nd}$ container, 30.48 g of squalene were mixed with 4.52 g of Montane™80 under agitation at ambient temperature. This oily phase had a weight of 35 g.

When both phases were homogeneous, 29.11 g of the oily phase was incorporated into the aqueous phase. The mixture was then gently agitated, and put in an oily bath at 80-90° C., under still gentle agitation (300 rpm). When the mixture reached 75° C., the emulsion was taken out of the oily bath and put on ice, while agitation was maintained at about 250 rpm. When the temperature of the mixture returned to ambient temperature, a homogeneous thermoreversible oil-in-water emulsion was obtained, in which more than 90% of the population by volume of the oil droplets had a size ≤200 nm and in which the composition by weight was as follows:
32.5% of squalene,
6.18% of ceteareth-12 (Eumulgin™B1),
4.82% of sorbitan monooleate (Montane™80),
6% of mannitol
0.026% of E6020.
50.5% of PBS This stock solution was then diluted at 1/6.5 by phosphate buffer (1×) to obtain an emulsion having 5% squalene and 40 µg/ml of E6020.

(iii) About 5 minutes to 1 hour in advance of the applicable immunization, antigen samples (10 µg of antigen suspended in 25 µl buffer) was gently mixed with 25 µl of adjuvant. Volume of composition inoculated was 50 µl.

The composition according to the present invention was compared to a positive and a negative control; the positive control comprised MOMP antigen and Montanide ISA 720 (obtained from Seppic) and CpG 1826 (obtained from Coley Pharmaceutical), and the negative control lacked MOMP antigen but was comprised of Ovalbumin and Montanide/CpG. The volume inoculated of the control compositions was 50 µl and comprised 10 µg CpG, with the ratio (v/v) of antigen (i.e., MOMP or albumin)+CpG: Montanide being 30:70.

Each composition was tested in a group of 13 BALB/c female mice, 3 weeks-old. The mice were administered the applicable composition 3 times, with a 2 week interval between each administration. Compositions were administered via the intramuscular route, in the 2 hind leg muscles.

Blood was collected by periorbital or heart puncture, and genital samples were collected by washing the vagina twice with 20 µl of PBS (pH 7.2). The immunoassays were performed using pooled sera or pooled vaginal washes from each group.

The antibody titers were determined using an enzyme-linked immunosorbent assay (ELISA). The following class or subclass-specific antibodies were assessed: IgG, IgG1, IgG2a, IgG3, IgA and IgM.

The in vitro neutralization assay was performed as follows: The assay utilized 96 well round bottom plates. Dilutions of each serum sample were prepared using PBS and 5% guinea pig sera (or 5% rabbit complement, Sigma). Into each dilution sample well, 1500 IFU/50 µl of EBs from $C.$ $trachomatis$ (diluted in PBS+5% guinea pig sera just prior to use), was added and the mixtures were incubated at 37° C. for 45 minutes with gentle rocking. A 96 well plate containing a HeLa cell monolayer (of HeLa cells seeded at $5\times10^4$ cells/well, about 24 hours earlier) was prepared and 50 µl of each dilution sample was transferred to sample wells in the HeLa cell monolayer plate. The plate was centrifuged for 60 minutes at room temperature at 1800 rpm. DMEM with L-glutamine and sodium pyruvate (Invitrogen) supplemented with 1 µg/ml cyclohexamide was added to each sample well and plates were incubated at 35° C. with 5% $CO_2$ for 44-48 hours. As controls, dilutions of EBs alone and dilutions of PBS+5% guinea pig sera alone were also prepared and added to specific wells of the HeLa cell plate.

Inclusion bodies were stained and the 50% neutralization titre was determined by calculating the value of percent neutralization for each of the sample dilutions by applying the formula, (IFU prebleed−IFU bleed)/IFU prebleed×100. Alternatively, the value could be determined by taking the average of the control samples with EBs alone in place of prebleed IFU. For each sample, the 50% neutralization titre is the lowest dilution with a value greater or equal to 50% (e.g., if a 1:400 dilution had 71% neutralization and a 1:800 had 34% neutralization, the 50% neutralization titre of that sample was 400).

10 mice per group were challenged in the left ovarian bursae 30 days after the last i.m. boost. The animals were anesthetized, and a lateral abdominal incision was made, which received $10^5$ IFU of MOMP in 20 µl of SPG (0.2M sucrose, 0.02M sodium phosphate [pH 7.2], and 0.005M glutamic acid). The course of the infection was followed with weekly vaginal cultures. Vaginal swabs were collected and cultured at 7-day intervals for a period of 6 weeks following the genital challenge. The swabs were wortexed in 200 µl of sterile sucrose-phosphate-glutamic acid medium, and 2 aliquots from each specimen (100 and 10 µl) were inoculated into McCoy cells grown in 48-well plates with centrifugation at 1,000×g for 1 h at room temperature. Following incubation at 37° C. for 30 h, the chlamydial inclusions were stained (see Table 4).

Six weeks after challenge, mice were mated twice. Pregnancy was assessed by determining the weight of each mouse. Mice that gained 7 to 10 g of weight by, or before, 18 days post-mating were considered to be pregnant. These mice were euthanized, and the number of embryos in each uterine horn was counted.

The results obtained are summarized in the following tables.

TABLE 1

Antibody titers in the sera the day before genital challenge

C. trachomatis MoPn-specific ELISA antibody titers

|  | IgG | IgG1 | IgG2a | IgG2b | IgG3 | IgA | IgM |
|---|---|---|---|---|---|---|---|
| Ova + CpG + Montanide | <100 | <100 | <100 | <100 | <100 | <100 | <100 |
| Ag + CpG + Montanide | 25,600 | 12,800 | 204,800 | 12,800 | 12,800 | 400 | <100 |
| Ag + Adjuvant invention | 51,200 | 12,800 | 102,400 | 25,600 | 12,800 | 1,600 | <100 |

(endpoint dilution ELISA not a serum dilution ELISA)

TABLE 2

Antibody titers in the vaginal washes before genital challenge

|  | IgG | IgA |
|---|---|---|
| Ova + CpG + Montanide | <10 | <10 |
| Ag + CpG + Montanide | 320 | <10 |
| Ag + Adjuvant invention | 640 | <10 |

TABLE 3

Serum neutralizing titers.

| Ova + CpG + Montanide | 0 |
|---|---|
| Ag + CpG + Montanide | 1,000 |
| Ag + Adjuvant invention | 1,000 |

TABLE 4

Results of vaginal culture

|  | Mean N° of MoPn IFU shed per week | | | | | | Total Nr. of mice that |
|---|---|---|---|---|---|---|---|
|  | Wk 1 | Wk 2 | Wk 3 | Wk 4 | Wk 5 | Wk 6 | Shed in 6 weeks |
| Ova + CpG + Montanide | 30 | 432 | 6239 | 135 | 0 | 0 | 7/10 |
| Ag + CpG + Montanide | 4 | 9 | 233 | 0 | 0 | 0 | 4/10 |
| Ag + Adjuvant invention | 1 | 3 | 0 | 0 | 0 | 0 | 1/10 |

TABLE 5

Results of fertility studies

|  | Total N° of mice fertile in both uterine horns |
|---|---|
| Ova + CpG + Montanide | 1/10 |
| Ag + CpG + Montanide | 8/9 |
| Ag + Adjuvant invention | 8/10 |

These data show that the evaluated immunogenic composition comprising MOMP and the adjuvant of the invention elicited both a Th1 biased immune response and neutralizing antibodies. This composition of the present invention was also able to protect against infection as shown by the significantly reduced bacterial shedding seen in challenged mice, and the fertility of the mice which received it.

Example 3

Immunization compositions of the present invention were tested to assess their ability to induce TH1 oriented cytokines and protect mice from overt genital infection in a low dose challenge model (i.e. intrabursal challenge model).

EB-MoPn MOMP antigen was prepared from MoPn substantially as described in Example 1. The adjuvants used in this example were prepared in the following way:

The adjuvant ADJ.A comprising E6020 and a squalene emulsion as a carrier was prepared in a manner substantially similar to that described in Example 2

Another adjuvant according to the present invention was also prepared which comprised ADJ.A and another immunostimulant which is a Toll-like receptor agonist 7/8. This Toll-like receptor 7/8 (Invivogen) was in flasks containing 500 µg of a imidazoquinoline product (lots 25-20-848 and 25-17-848). The content of each of these 2 flasks was diluted with ethanol to give a solution of TLR7/8 of 5 mg/ml.

The adjuvant composition was prepared by mixing 3 ml of ADJ.A with 0.12 ml of the solution comprising 5 mg/ml of TLR7/8 to give an adjuvant composition with the following formulation:

5% squalene
0.95% Eumulgin B1
0.74% Dehymuls SMO
0.92% mannitol
0.01593% E6020
0.01923% TLR 7/8 agonist.

A control adjuvant consisting of the squalene emulsion (ADJ.SQ) and the imidazoquinoline product (TLR 7/8 agonist) was also prepared in a manner substantially similar to that described in Example 2 for the preparation of the adjuvant emulsion comprising E6020 with the exception that the imidazoquinoline product (Invivogen) at a concentration of 200 µg/ml was included as opposed to E6020.

About 5 minutes to 1 hour in advance of the applicable immunization, antigen samples (10 μg of antigen suspended in 25 μl buffer) were gently mixed with 25 μl of adjuvant. Volume of composition inoculated was 50 μl. A negative control (i.e., a composition comprising Ovalbumin and emulsion+a TLR 7/8 agonist) with which the composition according to the present invention was compared, was prepared and was used to inoculate applicable mice (50 μl, comprising 10 μg of Ovalbumin suspended in 25 μl of buffer with 25 μl control adjuvant).

Each composition was tested in a group of 15 BALB/c female mice, 3 weeks of age at the time of 1st immunization. Mice were immunized 3 times, at 2 weeks intervals, intramuscularly, in the two hind leg muscles.

Samples of blood and vaginal bacterial shedding were collected before each immunization, twice before intrabursal challenge and a number of times post-challenge (i.e. on days 7, 27 and 41 post-challenge). Blood was collected by periorbital or heart puncture, and vaginal bacterial samples were collected by washing the vagina twice with 20 μl of PBS (pH 7.2). Vaginal swabs were collected for culturing on days 6, 12, 15, 20, 25, 35 and 42 post-challenge. The day before challenge, LPA and cytokines were performed on 3 mice from each group. All immunoassays were performed with sera or vaginal washes pooled from each group.

Antibody titers of specific classes or subclasses (i.e. IgG, IgG1, IgG2a, IgG3, IgA and IgM) were determined using ELISA. The in-vitro neutralization assay was performed as described above in Example No. 2. Bacterial shedding in vaginal washes was measured by titration in cell culture and Q-PCR. The T cell proliferation response the day before challenge was measured using a lymphocyte proliferation assay conducted substantially as follows: The spleens and inguinal and iliac lymph nodes of 2 to 4 mice from each group were collected, teased and splenocytes enriched for T-cells were prepared by passing cells over a nylon wool column. Accessory cells for antigen presentation were prepared by irradiating (3,000 rads; 137 Cs) syngeneic unseparated spleen cells and incubating them with various ratios of *C. trachomatis* EB. As a positive control, cells were stimulated with Concanavalin A (Con A) and as negative controls, cells were stimulated with Ovalbumin or HeLa cell extracts and tissue culture media. At the end of 4 days of incubation, 1.0 μCi of [methyl-3H] thymidine (47 Ci/mmol; Amersham, Arlington Heights, Ill.) in 25 μl of RPMI 1640 was added per well, and the incorporation of 3H was measured using a scintillation counter (Beckham Instruments, Fullerton, Calif.).

The in vitro cytokine (i.e., IL-10, IL-6 and IFN-γ) production by splenic T cells the day before challenge was also measured. Cytokine levels was determined by testing supernatant samples from splenic T cells stimulated as described above with commercial kits (e.g., BDPharMingen, San Diego, Calif.).

Mice were subsequently challenged in the left ovarian bursae 30 days after the last i.m. immunization. The animals were anesthetized (using xylazine/ketamine), a lateral abdominal incision was made, and $10^5$ IFU of CT-MoPn (MOMP) in 20 μl of SPG (0.2M sucrose, 0.02M sodium phosphate [pH 7.2] and 0.005M glutamic acid) was applied.

The results obtained following the three immunizations are set out in the tables below.

TABLE 6

Antibody titers in the sera the day before genital challenge

| | *C. trachomatis* MoPn-specific ELISA antibody titers | | | | | |
|---|---|---|---|---|---|---|
| | IgG | IgG1 | IgG2a | IgG2b | IgG3 | IgA |
| Ova + ADJ.A (negative control) | <0.1 | <0.1 | <0.1 | <0.1 | <0.1 | <0.1 |
| MoPn EB-MOMP + ADJ.A | 409.6 | 102.4 | 102.4 | 204.8 | 204.8 | 0.8 |
| MoPn EB-MOMP + ADJ.SQ + TLR7/8 | 102.4 | 204.8 | 51.2 | 51.2 | 51.2 | 0.4 |
| MoPn EB-MOMP + ADJ.A + TLR7/8 | 204.8 | 51.2 | 51.2 | 102.4 | 102.4 | 0.4 |

(endpoint dilution ELISA, not a serum dilution ELISA)

TABLE 7

Antibody titers in the vaginal washes before genital challenge

| | IgG | IgA |
|---|---|---|
| Ova + ADJ.A (negative control) | <10 | <10 |
| MoPn EB-MOMP + ADJ.A | 640 | 40 |
| MoPn EB-MOMP + ADJ.SQ + TLR7/8 | 40 | <10 |
| MoPn EB-MOMP + ADJ.A + TLR7/8 | 640 | 40 |

TABLE 8

Serum neutralizing titers.

| Ova + ADJ.A (negative control) | <50 |
|---|---|
| MoPn EB-MOMP + ADJ.A | 1,250 |
| MoPn EB-MOMP + ADJ.SQ + TLR7/8 | 250 |
| MoPn EB-MOMP + ADJ.A + TLR7/8 | 1,250 |

TABLE 9

Results of vaginal culture

| | Mean N° of MoPn IFU shed per week | | | | | | Total No. of mice that |
|---|---|---|---|---|---|---|---|
| | Wk 1 | Wk 2 | Wk 3 | Wk 4 | Wk 5 | Wk 6 | shed in 6 weeks |
| Ova + ADJ. A | 21,668 ± 11,227 | 1,225 ± 1,203 | 0 | 0 | 0 | 0 | 10/12 (83%) |
| MoPn EB-MOMP + ADJ.A | 61 ± 47 | 9,470 ± 4,980 | 1 ± 0 | 0 | 0 | 0 | 7/12 (58%) |
| MoPn EB-MOMP + ADJ.SQ + TLR7/8 | 2,849 ± 1,981 | 2,413 ± 2,052 | 1 ± 0 | 1 ± 0 | 0 | 0 | 8/12 (66%) |
| MoPn EB-MOMP + ADJ.A + TLR7/8 | 13,470 ± 13,343 | 245 ± 241 | 1,952 ± 1,806 | 0 | 0 | 0 | 4/12 (33%) |

TABLE 10

T cell responses the day before challenge

T cell proliferation response mean ± 1 SD ($10^3$ cpm)

| | EB[a] | Ovalbumin[b] | Con A[c] | Medium |
|---|---|---|---|---|
| Ova + ADJ.A | 0.96 ± 0.18 | 10.5 ± 1.4 | 61.0 ± 6.9 | 0.17 ± 0.03 |
| MoPn EB-MOMP + ADJ.A | 2.40 ± 1.40 | 0.18 ± 0.07 | 67.7 ± 16.5 | 0.15 ± 0.03 |
| MoPn EB-MOMP + ADJ.SQ + TLR7/8 | 3.53 ± 2.62 | 0.13 ± 0.06 | 44.6 ± 6.7 | 0.18 ± 0.06 |
| MoPn EB-MOMP + ADJ.A + TLR7/8 | 4.87 ± 1.83 | 0.24 ± 0.18 | 54.6 ± 3.8 | 0.13 ± 0.03 |

[a]UV-inactivated *C. trachomatis* MoPn EB were added at a 50:1 ratio to the APC
[b]Ovalbumin was added at a concentration of 10 µg/ml
[c]Concanavalin A (Con A) was added at a concentration of 5 µg/ml

TABLE 11

In vitro cytokine production by splenic T cells the day before challenge

In vitro cytokine production [IL-10 (pg/ml)]

| | EB[a] | Ovalbumin[b] | Con A[c] | Medium |
|---|---|---|---|---|
| Ova + ADJ.A | 257 ± 4 | 159 ± 13 | 1,246 ± 28 | 6 ± 0 |
| MoPn EB-MOMP + ADJ.A | 361 ± 3 | 17 ± 16 | 1,181 ± 38 | 19 ± 1 |
| MoPn EB-MOMP + ADJ.SQ + TLR7/8 | 536 ± 80 | 25 ± 28 | 1,257 ± 52 | 32 ± 17 |
| MoPn EB-MOMP + ADJ.A + TLR7/8 | 444 ± 24 | 17 ± 17 | 1,344 ± 37 | 5 ± 0 |

[a]UV-inactivated *C. trachomatis* MoPn EB were added at a 50:1 ratio to the APC
[b]Ovalbumin was added at a concentration of 10 µg/ml
[c]Concanavalin A (Con A) was added at a concentration of 5 µg/ml

TABLE 12

In vitro cytokine production by splenic T cells the day before challenge

In vitro cytokine production [IL-6 (pg/ml)]

| | EB[a] | Ovalbumin[b] | Con A[c] | Medium |
|---|---|---|---|---|
| Ova + ADJ.A | 838 ± 124 | 1218 ± 79 | 1,255 ± 32 | 445 ± 114 |
| MoPn EB-MOMP + ADJ.A | 1,390 ± 22 | 16 ± 0 | 857 ± 14 | 15 ± 4 |
| MoPn EB-MOMP + ADJ.SQ + TLR7/8 | 1,786 ± 97 | 23 ± 1 | 1,366 ± 29 | 13 ± 3 |
| MoPn EB-MOMP + ADJ.A + TLR7/8 | 1,384 ± 21 | 23 ± 2 | 1,390 ± 43 | 18 ± 1 |

[a]UV-inactivated *C. trachomatis* MoPn EB were added at a 10:1 ratio to the APC
[b]Ovalbumin was added at a concentration of 10 µg/ml
[c]Concanavalin A (Con A) was added at a concentration of 5 µg/ml

TABLE 13

In vitro cytokine production by splenic T cells the day before challenge

In vitro cytokine production [IFN-γ (pg/ml)]

| | EB[a] | Ovalbumin[b] | Con A[c] | Medium |
|---|---|---|---|---|
| Ova + ADJ.A | 5,636 ± 3,822 | 11,531 ± 491 | 11,124 ± 34 | 557 ± 394 |
| MoPn EB-MOMP + ADJ.A | 12,228 ± 958 | 445 ± 6 | 11,609 ± 81 | 356 ± 24 |
| MoPn EB-MOMP + ADJ.SQ + TLR7/8 | 10,791 ± 309 | 336 ± 3 | 11,807 ± 199 | 289 ± 39 |
| MoPn EB-MOMP + ADJ.A + TLR7/8 | 11,218 ± 30 | 405 ± 118 | 11,888 ± 121 | 311 ± 118 |

[a]UV-inactivated *C. trachomatis* MoPn EB were added at a 10:1 ratio to the APC
[b]Ovalbumin was added at a concentration of 10 µg/ml
[c]Concanavalin A (Con A) was added at a concentration of 5 µg/ml High IgG antibody titers in serum were observed in the groups immunized with adjuvanted MOMP. A balanced Th1/Th2 response was observed in mice immunized with native MOMP (i.e., EB MOMP) adjuvanted with the adjuvant of the invention (ADJ.A). A predominant Th2 response was elicited in mice immunized with native MOMP and ADJ.SQ+TLR7/8. High neutralizing serum antibody titers and high IgG and IgA antibody titers in the vagina were observed in animals immunized with native MOMP adjuvanted with ADJ.A. Protection from vaginal shedding was observed in the two groups immunized with native MOMP and the two adjuvants. According to the present invention, the strongest immune response and the highest titre of IFN-γ were elicited by native MOMP adjuvanted with ADJ.A adjuvant. Native MOMP adjuvanted with ADJ.SQ+TLR 7/8 elicited higher levels of the Th2 cytokines, IL-10 and IL-6.

Example 4

The preceding Examples described studies utilizing native MOMP isolated from the *Chlamydia* MoPn strain (mouse pneumonitis). To assess immunogenic compositions comprising MOMP derived from *Chlamydia* strains that afflict humans, sample lots of MOMP from a number of *C. trachomatis* serovars were prepared. In the studies described in Examples 5 to 8 bulk lots of recombinant MOMP (herein referred to as rMOMP) were utilized to prepare immunogenic compositions. The rMOMP lots utilized in these studies were prepared substantially in accordance with the process described in this Example. Although the procedure described relates to the cloning and preparation of rMOMP from *C. trachomatis* serovar E, rMOMP from any *C. trachomatis* serovar and from any serovar of any other *Chlamydia* species may be prepared substantially in accordance to this process.

The nucleotide sequence of full-length MOMP (but lacking signal sequence) was amplified from genomic DNA of *C. trachomatis* serovar E strain BOUR (ATCC #VR-348B) and the resulting PCR product was ligated into pET24b(+). The ligation mixture was transformed into chemically competent *E. Coli* DH5α. Single colonies from positive clones were cultured overnight and plasmid DNA was isolated using a QIAprep Spin Miniprep Kit. A clone with the correct size fragment was selected and DNA sequence analysis confirmed presence of correct MOMP DNA sequence (SEQ ID NO:1). The predicted amino acid sequence of the inserted coding sequence is set out as SEQ ID NO: 2. Plasmid DNA from clone was transformed into chemically competent *E. Coli* BL21(DE3) cells and a single colony was cultured to assess protein expression. MOMP protein expression was induced with 1 mM IPTG, confirmed by SDS-PAGE and Western analysis (and was considered sufficient for downstream protein purification). Glycerol stocks were made from the overnight culture. Recombinant MOMP from *C. trachomatis* serovars D, F, J, Ia and MoPn were cloned in a substantially similar manner. In each case, DNA sequence analysis was performed confirming the sequence of the insert was correct (SEQ ID NOs: 3 (serovar F), 5 (serovar J), 7 (serovar Ia), 9 (serovar D)). The predicted amino acid sequence of the inserted coding sequences are set out as SEQ ID NOs: 4 (serovar F), 6 (serovar J), 8 (serovar Ia), 10 (serovar D), 11 (MoPn)).

Fermentation was conducted using a 20 L fermenter and an IB fraction/pellet of the recombinant protein was prepared and the IB fraction was subjected to a purification and folding process which is described further below.

Purification: The IB fraction/pellet was mixed in a solubilization buffer (of 25 mM KCl, 25 mM NaOH and 8 M urea at pH 12.5) at a ratio of approximately 20 mL/g wet weight of IB pellet. The mass of Ser E MOMP IB pellet used was about 118.5 g. The pH was adjusted with NaOH following resuspension of the pellet to about 12.5, and the mixture was incubated at room temperature with gentle agitation for 40 min. Following incubation, the mixture was subjected to centrifugation (10397 g, 20 min, 4° C.). The supernatant, containing solubilized rMOMP, was mixed with an equal volume of buffer containing 50 mM Tris-HCl pH 7.0, and 8M urea, and the pH was adjusted with 6 N HCl to pH 8.5. DTT was added to the solution to achieve a concentration of 10 mM. The conductivity of the solution was checked with a conductivity meter, and was reduced to 2.0-2.5 mS by dilution with 50 mM Tris-HCL pH 8.5, 8 M urea, 1 mM EDTA. The solution was filtered and the final volume was 5.5 L.

Chromatographic operations were carried out using an AKTA Pilot (G.E. Healthcare) chromatography unit with a column (BPG100, G.E. Healthcare) packed with Pall Bio-Sepra Q Ceramic HyperD F anion exchange sorbent. The column was washed, regenerated, and equilibrated. Following column equilibration (using an equilibration buffer of 50 mM Tris-HCl, pH 8.5; 8 M urea; 1 mM EDTA), 5 L of the starting material was loaded onto the column. The chase volume (with equilibration buffer) was about 4 CV, and this was followed by a wash step at about 5 CV with equilibration buffer to which was added NaCl to 25 mM. Elution was performed with 4.5 CVs equilibration buffer containing 75 mM NaCl. A suitable range of NaCl concentration in wash buffer is 20 mM-40 mM and a preferred concentration is 20 mM NaCl. Elution was performed with 4.5 CVs equilibration buffer containing 75 mM NaCl. A suitable range of NaCl concentration in elution buffer is 40 mM-90 mM and a preferred concentration is 40 mM NaCl.

In subsequent studies, to increase the purity of the resultant rMOMP protein an additional purification step using CEX chromatography in the flow-through mode was added upstream of the AEX chromatographic step. The CEX step was conducted at a pH of 5.5-6 after which the solution pH was adjusted to 8.5 for the AEX step. However, since the CEX step is conducted at a pH of approximately 5.5 which is close to the pI of rMOMP (~4.8), a second pH shock step before the AEX step may also be included to avoid the development of soluble aggregates.

Prior to diafiltration, 3.9 g DTT was added to the purified rMOMP pool, resulting in a concentration of 10 mM. To this was added 2.5 L of 1 M 1-arginine, followed by 2.5 L 6% v/v NLS; each of these solutions having been prepared in a buffer containing 50 mM Tris-HCl, pH 8. The rMOMP-arginine-NLS mixture was then mixed at room temperature.

MOMP Folding Procedure

The purified rMOMP was treated with DTT, arginine, and NLS, followed by a two part TFF operation which induces folding and reduces residual NLS detergent. The refolding procedure involved the reduction of rMOMP's disulfide bonds with DTT (e.g., about 10 mM DTT), the addition of the molecular chaperone, 1-arginine, (e.g. about 333 mM), and the addition of the detergent n-lauroyl sarcosine (NLS), (e.g. about 2% NLS). The mixture was then subjected to a two-part TFF operation, which is briefly described below.

1. Following the addition of the arginine and NLS solutions, the MOMP-arginine-NLS mixture (e.g., about 7.5 L) was concentrated by TFF (using TFF filtration apparatus, Sartocon 2Plus unit with Sartorius Hydrosart cassettes) until it reached the original rMOMP sample volume (i.e., approximately a threefold reduction).

2. TFF was operated in the diafiltration mode for approximately five volumes of Tris buffer (50 mM Tris-HCl pH 8).

3. The mixture was diluted 1:3 with Tris buffer (50 mM Tris-HCl pH 8), and subjected to a further (approximately) 5 volumes of diafiltration with Tris buffer containing 0.1% v/v NLS, while maintaining the diluted volume.

4. The mixture was concentrated (approximately) threefold by TFF (e.g. to about 1.2 L), recovered from the TFF device, and EDTA was added to achieve a concentration of 1 mM.

The TFF operations had a total elapsed time of ~2.5 h, similar to the target time established for lab scale TFF folding (2-4 h). Previous investigations found that prolonged TFF folding, originally adopted to reduce shear forces and provide a more gentle environment, was in fact deleterious to the folding attempt, in which the development of aggregated protein as indicated by BN-PAGE gel analysis occurred.

The folding process was considered successful if the resulting protein product was soluble in aqueous buffers at >1 mg/mL, and the characteristic ladder pattern in BN-PAGE gels was evident. The presence of discrete bands of MOMP protein over a range of molecular weights is indicative of multimeric units (somewhat analogous to the putative trimeric state found with the native protein). FIG. 1 illustrates BN-PAGE gel patterns with the pilot scale lot and three lots of lab scale Ser E rMOMP protein. Patterns are similar, with the presence of a ladder consisting of at least four bands of similar apparent molecular weight. Additionally, there is little evidence of monomeric rMOMP, normally seen just below the 66 kDa marker (not shown).

The purity of the final protein product was assessed by scanning densitometry of SDS-PAGE gels. FIG. 2 shows an image of an SDS-PAGE gel for the pilot Ser E lot. Protein purity was assessed as approximately 88% by scanning densitometry, with a low molecular weight band accounting for 6% of the total protein. The percentage assessed may be an underestimate of MOMP purity as putative MOMP related bands on the gel were not identified. The calculated yield was approximately 4.8 g. The concentration of residual components was assessed and considered well within appropriate limits: endotoxin content was 0.005 EU/μg protein, and residual NLS was 0.49% (i.e., approximately 0.24% at 1 mg/mL).

Example 5

Immunogenic compositions comprising rMOMP adjuvanted with one of several adjuvants were evaluated in an animal model.

Groups of female BALB/c mice (15 per group) (Charles River) were immunized intramuscularly three times, at approximately 3 week intervals with 50 μl of the applicable composition (as noted in Table 14). The mice were approximately 7-8 weeks of age at the time of the $1^{st}$ immunization. As a control, 4 groups were administered compositions of adjuvanted Ovalbumin. Pre-bleed samples were obtained approximately 4 days before the first immunization.

TABLE 14

| | | Vaccine component and volume to inoculate per mouse | |
|---|---|---|---|
| Grp. | No. mice | Vol. injected/mouse | Composition (antigen + adjuvant) |
| A | 15 | 50 μl | OVA + ADJ.A |
| B | 15 | 50 μl | OVA + ADJ.SQ |
| C | 15 | 50 μl | OVA + aluminum hydroxide (Alhydrogel) |
| D | 14 | 50 μl | OVA + Montanide/CpG |
| E | 15 | 50 μl | rMOMP alone |
| F | 15 | 50 μl | rMOMP + ADJ.A |

TABLE 14-continued

| | | Vaccine component and volume to inoculate per mouse | |
|---|---|---|---|
| Grp. | No. mice | Vol. injected/mouse | Composition (antigen + adjuvant) |
| G | 15 | 50 μl | rMOMP + ADJ.SQ |
| H | 15 | 50 μl | rMOMP + aluminum hydroxide (Alhydrogel) (50 μg/dose) |
| I | 14 | 50 μl | rMOMP + Montanide/CpG (10 μg/dose); PBS |

Formulations were freshly prepared before each immunization. Antigens, buffers and adjuvants were stored at 4° C. First, antigen (i.e., Ovalbumin or rMOMP) 15 μg/dose was diluted in buffer 50 mM Tris, pH 8.0, 0.1% NLS (30 μl/dose). To this mixture the applicable adjuvant was added, plus buffer when necessary to obtain an immunization dose of 50 μl.

Aluminum adjuvant used is the one called Alhydrogel which is aluminum oxyhydroxyde or AlOOH, at a concentration of 9.9 mg/ml. The final quantity of aluminum in the immunization doses is 50 μg/dose ADJ.A was prepared by diluting at 1/5 the stock solution prepared in Example 2 with PBS, so as to get an emulsion comprising 6.5% squalene.

ADJ.SQ was prepared from a stock solution prepared as ADJ.A's one with the exception that no E6020 product was included. Then, this stock solution of ADJ.SQ was diluted at 1/6.5 with PBS to get an emulsion comprising 5% squalene.

As the concentration of squalene and surfactants were higher in ADJ.A than in ADJ.SQ, the preparation of the formulations utilized for the immunizations were different for both adjuvants to obtain the same final concentration of 2.5% squalene in the immunization doses (although, inadvertently, for the $1^{st}$ immunization, the final concentration of squalene in the ADJ.SQ group was 2%).

One mouse from group B was found dead 4 days before the $3^{rd}$ immunization (and was bled out).

Sera were collected from immunized animals about 2 weeks after the $3^{rd}$ immunization and were pooled for each group to assess antibody response by ELISA.

Mice were euthanized and their spleens removed aseptically. Single cell suspensions were prepared. Splenocytes from mice belonging to the same group were pooled and were pelleted by centrifugation. Erythrocytes in the suspension were lysed. The cell suspension was transferred to another tube and centrifuged to pellet the cells. Process was repeated to ensure that most of the erythrocytes were lysed. The cell pellet was resuspended, cells were counted and plated. Cells were stimulated with Ovalbumin, rMOMP, UV-inactivated *C. trachomatis* MoPn EB MOMP, or PMA.

Isotyping analysis of the antibody profile generated was done using ELISA based reagents. Induction of Th1/Th2 responses was analyzed by quantifying the antigen-specific IgG2a (Th1) and IgG1 (Th2) antibody response and by measuring levels of cytokines (e.g., IFN-γ (Th1), interleukin-10 (Th2)) in antigen-stimulated splenocyte culture (i.e., by assaying in vitro cytokine production by splenic T cells).

A summary of the ELISA results and the cytokine profile by MSD analysis are set out in Tables 15 and 16.

TABLE 15

| | ELISA Titre | | | | | | % Neutralizing Mice 0 | Average Titre | Range Titre (positive mice) |
|---|---|---|---|---|---|---|---|---|---|
| | Total IgG Avg | sd | IgG1 Avg | sd | IgG2a Avg | sd | | | |
| OVA + ADJ.A | 50 | 0 | 50 | 0 | 50 | 0 | 0 | NA | NA |
| OVA + ADJ.SQ | 50 | 0 | 50 | 0 | 50 | 0 | 0 | NA | NA |
| OVA + Alum (AlOOH) | 50 | 0 | 50 | 0 | 50 | 0 | 0 | NA | NA |
| OVA + CpG/Montanide | 106 | 160 | 50 | 0 | 50 | 0 | 0 | NA | NA |
| rMOMP alone | 1437 | 3316 | 317 | 820 | 50 | 0 | 0 | NA | NA |
| rMOMP + ADJ.A | 1621333 | 1482613 | 45070 | 102076 | 17767 | 28802 | 33 | 65 | 25-100 |
| rMOMP + ADJ.SQ | 421547 | 815814 | 11067 | 17389 | 50 | 0 | 0 | NA | NA |
| rMOMP + Alum | 2427 | 3104 | 93 | 100 | 50 | 0 | 0 | NA | NA |
| rMOMP + CpG/Montanide | 310613 | 419299 | 7397 | 8790 | 23680 | 26795 | 40 | 38 | 25-100 |

TABLE 16

| | MSD Analysis | | | | | |
|---|---|---|---|---|---|---|
| | INFγ | IL-10 | IL-4 | IL-5 | IL-2 | IL-12(p70) |
| OVA + ADJ.A | 845.5 | 2890.1 | 295.0 | 3472.5 | 1656.6 | 99.7 |
| OVA + ADJ.SQ | 323.1 | 244.4 | 70.2 | 1475.7 | 1116.7 | 49.7 |
| OVA + Alum (AlOOH) | 816.0 | 267.8 | 79.8 | 194.1 | 1729.9 | 101.6 |
| OVA + CpG/Montanide | 316.8 | 95.6 | 38.7 | 68.8 | 1119.3 | 24.4 |
| rMOMP alone | 930.5 | 9343.5 | 392.2 | 8975.5 | 1000.0 | 146.6 |
| rMOMP + ADJ.A | 14747.1 | 18601.1 | 1365.4 | 13504.6 | 4231.4 | 857.0 |
| rMOMP + ADJ.SQ | 1364.1 | 1113095.5 | 1189.8 | 40230.4 | 830.6 | 896.6 |
| rMOMP + Alum | 1440.9 | 5222.7 | 501.9 | 8194.6 | 1897.6 | 301.9 |
| rMOMP + CpG/Montanide | 3818.3 | 6349.9 | 810.6 | 266.1 | 1147.3 | 258.4 |

In accordance to the EB-ELISA (antibody) results, the immunogenic composition with unadjuvanted rMOMP was weakly immunogenic and of the IgG classes tested, solely IgG1 was detectable. The carrier Aluminum hydroxide was not an effective adjuvant for rMOMP. Adjuvanting rMOMP with the other carrier, ADJ.SQ, elicited strong immune responses (i.e., total IgG) but the response was pre-dominantly a Th2 type, not a Th1/Th2 balanced response (e.g., no detectable IgG2a was elicited). Adjuvanting rMOMP with Adjuvant, ADJ.A (an adjuvant according to the present invention) or CpG/Montanide elicited strong immune responses with balanced Th1/Th2 subclasses, at comparable levels. In addition, Adjuvant of the invention switched the immune profile induced by un-adjuvanted rMOMP from an IgG1 only, to a balanced Th1/Th2 antibody response.

The capacity of the sera from immunized mice to neutralize C. trachomatis serovar E was assessed with an in vitro neutralization assay against serovar E EBs. The assay conducted was substantially similar to that described in Example 2, with the EBs used in this case coming from C. trachomatis serovar E as opposed from C. trachomatis MoPn. A summary of the results from the neutralization assay against SerE are set out in Table 15.

These data show that neutralizing antibodies were detected only in the group immunized with compositions comprising rMOMP and ADJ.A. Although strong antibody responses (of predominantly IgG1 subclass) were stimulated in mice immunized with compositions comprising rMOMP and ADJ.SQ, the sera from these mice had no detectable neutralizing capacity. Of the compositions administered, those including rMOMP adjuvanted with ADJ.A or CpG/Montanide stimulated neutralizing antibodies to serovar E.

This test confirms that compositions comprising recombinant MOMP derived from a Chlamydial strain afflicting humans (e.g., C. trachomatis) gave results as good as the ones obtained with an adjuvant of the prior art (i.e., CpG/Montanide), but with the advantage of avoiding the use of a water-in-oil emulsion.

Example 6

Immunogenic compositions comprising rMOMP (2 different doses) adjuvanted with an adjuvant according to the invention with varying concentrations of E6020, were evaluated in an animal model.

Groups of female CDI mice (6 to 12 per group) (Charles River) were immunized intramuscularly on three separate occasions (at about 3 week intervals) with 50 µl of the applicable composition (as noted in Table 17). Two doses of antigen (rMOMP) were used, 10 µg and 25 µg. E6020 were tested at 3 doses, 0.25 µg, 0.5 µg and 1 µg. A group of mice was also tested with one carrier alone, this being the group with ADJ.SQ considered as 0 µg of E6020. CD1 is an outbred strain, in contrast to Balb/C which is an inbred strain. This outbred strain provides a more robust model and is more akin to humans (e.g., more diversified). The mice were approximately 7-8 weeks of age at the time of the 1$^{st}$ immunization. As a negative control, groups E and F were administered compositions of adjuvanted Ovalbumin.

TABLE 17

Vaccine component and volume to inoculate per mouse

| Grp | No. mice | Vol. injected/mouse | Composition (antigen + adjuvant) | Ratio of antigen:E6020 |
|---|---|---|---|---|
| A | 12 | 50 µl | JR3182 10 µg + ADJ.SQ | NA |
| B | 12 | 50 µl | JR3182 10 µg + ADJ.A (E6020 1 µg) | 10:1 |
| C | 12 | 50 µl | JR3182 10 µg + ADJ.A (E6020 0.5 µg) | 20:1 |
| D | 12 | 50 µl | JR3182 10 µg + ADJ.A (E6020 0.25 µg) | 40:1 |
| E | 6 | 50 µl | OVA 25 µg + ADJ.SQ | NA |
| F | 6 | 50 µl | OVA 25 µg ADJ.A (E6020 1 µg) | NA |
| G | 12 | 50 µl | JR3182 25 µg + ADJ.SQ | NA |
| H | 12 | 50 µl | JR3182 25 µg + ADJ.A (E6020 1 µg) | 25:1 |
| I | 12 | 50 µl | JR3182 25ug + ADJ.A (E6020 0.5 µg) | 50:1 |
| J | 12 | 50 µl | JR3182 25ug + ADJ.A (E6020 0.25 µg) | 100:1 |

Formulations were freshly prepared before each immunization. Proteins, buffers and adjuvant were stored at 4° C. Mixtures were prepared by diluting protein (Ovalbumin or rMOMP) in buffer (50 mM Tris, pH 8.0, 0.1% NLS), 25 µl/dose and then adding to this mixture the applicable adjuvant. Mixtures including E6020 were vortexed on high for about 1 min. Prepared formulations were placed on ice until required.

The adjuvants used in the present example were prepared in the following manner: ADJ.SQ was prepared as previously described in Example 3; and, ADJ.A was prepared as described in Example 2, and diluted by ADJ.SQ to reach the requested concentration of E6020. This means that for Groups B, F and H, the ADJ.A used was the same as the one described in Example 2 having 5% squalene and 40 µg/ml of E6020. For Groups C and I, the ADJ.A used is the same as the one used for the preceding group but diluted once at ½ with ADJ. SQ to have a concentration of E6020 of 20 µg/ml. And for Groups D and J, the ADJ.A used was diluted once more at ½ by ADJ.SQ to have a concentration of E6020 which is 10 µg/ml.

Sera were collected from immunized animals about 2 weeks post-immunization and were pooled for each group to assess EB-specific antibodies by ELISA. One mouse from group F was found dead 2 days following the 2nd immunization (and was bled out).

Mice were euthanized and their spleens removed aseptically. Single cell suspensions were prepared. Splenocytes from mice belonging to the same group were pooled. The splenocytes were restimulated in vitro with rMOMP for 3 days. The culture supernatants were collected and the cytokine production was measured for IFN-γ, IL-4, IL-5, and IL-10 and by MSD.

Isotyping analysis of the antibody profile generated was done using ELISA based reagents. Induction of Th1/Th2 responses was analyzed by quantifying the antigen-specific IgG2a (Th1) and IgG1 (Th2) antibody response and by measuring levels of cytokines (e.g., IFN-γ (Th1), interleukin-10 (Th2)) in antigen-stimulated splenocyte culture (i.e., by assaying in vitro cytokine production by splenic T cells).

The ability of the elicited antibodies to neutralize C. trachomatis serovar E was assessed by neutralization assay (performed substantially as described in Example 5). A summary of the ELISA titres neutralizing titres and cytokine profile by MSD analysis are set out in Table 18.

TABLE 18

| | Adjuvant | | Antigen | | Results | | | | | | | | |
|---|---|---|---|---|---|---|---|---|---|---|---|---|---|
| | Dose | | | Ag | Neutralizing | | ELISA & MSD Analysis | | | | | | |
| Grp. | E6020 (µg) | lot | Ag | Dose (µg) | Positive mice | Avg Titre | Total IgG | IgG1 | IgG2a | INF-g | IL-10 | IL-4 | IL-5 |
| E6020 + ADJ.SQ | | | | | | | | | | | | | |
| B | 1 | JR3182 | | 10 | 11/12 | 451 | 623467 | 3796 | 770742 | 14495 | 3836 | 84 | 1450 |
| C | 0.5 | | | 10 | 8/12 | 200 | 558967 | 19975 | 320300 | 19241 | 4788 | 86 | 2351 |
| D | 0.25 | | | 10 | 7/12 | 134 | 159733 | 5675 | 46283 | 17149 | 5728 | 94 | 3479 |
| H | 1 | | | 25 | 10/12 | 420 | 441600 | 7667 | 377096 | 14931 | 3739 | 80 | 1009 |
| I | 0.5 | | | 25 | 11/12 | 372 | 401033 | 8675 | 652433 | 14518 | 5196 | 123 | 2027 |
| J | 0.25 | | | 25 | 11/12 | 422 | 844600 | 12413 | 378200 | 10750 | 4458 | 91 | 2075 |
| F | 1 | | ova | 25 | NA | 12.5 | 50 | 50 | 50 | 148 | 159 | 6 | 55 |
| ADJ.SQ | | | | | | | | | | | | | |
| A | | | | 10 | 7/12 | 122 | 340267 | 3896 | 10992 | 2215 | 7726 | 87 | 4841 |
| G | | | | 25 | 8/12 | 200 | 298667 | 22938 | 48854 | 4451 | 4343 | 96 | 3646 |
| F | | | ova | 25 | NA | 12.5 | 50 | 50 | 50 | 357 | 364 | 9 | 36 |

Compositions of rMOMP adjuvanted with ADJ.SQ (i.e., lacking E6020) elicited levels of total IgG (including IgG1 and IgG2 subclasses) similar to those elicited with rMOMP adjuvanted with ADJ.A, however, the neutralizing capacity of the anti-sera was lower in comparison to anti-sera elicited by compositions comprising rMOMP adjuvanted with ADJ.A. These ADJ.SQ compositions stimulated a Th2-biased immune response (i.e., elicited high levels of Th2 cytokines and low levels of IFN-γ). The addition of E6020 shifted the immune response towards a Th1 type response.

Example 7

Immunogenic compositions comprising rMOMP adjuvanted with ADJ.A produced by one of several different processes.

Groups of female CDI mice (10 per group) (Charles River) were immunized intramuscularly on three separate occasions (at about 3 week intervals) with 50 µl of formulations comprising either 1 or 10 µg of rMOMP, and having 1 µg of E6020 with the carrier comprising a squalene emulsion. In this study, the process for preparing the adjuvant was prepared in one of several different ways: either the product E6020 was introduced in the aqueous phase before the emulsification took place, or it was introduced in the oily phase, or even in some cases, it was simply added to the emulsion. The adjuvant effect of E6020 in the rMOMP composition was similar irrespective of which of the three preparation methods was utilized. The three adjuvants tested elicited similar levels of antigen-specific total IgG, with both IgG1 and IgG2a subclasses, similar in vitro neutralizing capacity and similar cytokine production profiles.

Example 8

This example is related to immunogenic compositions comprising E6020 and aluminum hydroxide as a carrier.

Groups of female CDI mice (10 per group) (Charles River) were immunized intramuscularly on three separate occasions (at about 3 week intervals) with 50 µl of formulations comprising 10 µg of rMOMP and one of several adjuvants (i.e., ADJ.SQ, ADJ.A, Alum (aluminum hydroxide), and ADJ.B (an adjuvant comprising E6020+Alum (aluminum hydroxide))). Immunization doses were prepared by mixing 25 µl of the antigen solution (rMOMP in buffer (50 mM Tris pH 8.0+0.1% NLS)) with 25 µl of adjuvant.

The adjuvant according to the invention (ADJ.B, comprising E6020 and Alum) was prepared in the following manner:

Powder E6020 (EISAI) was diluted in ethanol to reach a concentration of about 12 mg/ml. 100 µl of this solution was then added to 1.9 ml of water which was maintained under agitation. The aqueous solution was then filtered and mixed with buffer PBS (10×) (9 volume of E6020 solution for 1 volume of PBS (10×) to get an aqueous solution of E6020 (with some ethanol) at about 0.5 mg/ml. To a Peni flask with 120 µl of this aqueous E6020 solution and 930 µl of PBS (1×) was added 450 µl of an aqueous suspension of AlOOH at a concentration of 8 mg/ml. This mixture was homogenized and vortexed for 10 seconds. The prepared adjuvant (ADJ.B) comprised 2.4 mg/ml of Aluminum and 40 µg/ml of E6020.

The ADJ. SQ adjuvant used in this example was prepared substantially as described in Example 3 and ADJ.A was prepared substantially as described in Example 2.

Collection of sera and splenocytes was done substantially as described in Example 6 and measurement of cytokine production and isotyping analysis was also performed substantially as described in that Example. The ability of the elicited antibodies to neutralize *C. trachomatis* serovar E was assessed by neutralization assay (performed substantially as described in Example 5). A summary of the ELISA titres, neutralizing titres and cytokine profile by MSD analysis are set out in Tables 19 and 20.

TABLE 19

| | ELISA Titre | | | | | | | | |
|---|---|---|---|---|---|---|---|---|---|
| | Total IgG Avg | sd | IgG1 Avg | sd | IgG2a Avg | sd | % Neutralizing Mice | Average Titre | t-test |
| rMOMP + ADJ.SQ | 79840 | 74271 | 42560 | 36821 | 30755 | 64745 | 20% | 80 | 0.028 |
| rMOMP + Alum | 3415 | 7857 | 1625 | 3957 | 205 | 490 | 0% | 13 | 0.015 |
| rMOMP + ADJ.A | 348160 | 506164 | 57765 | 79520 | 496650 | 1009398 | 90% | 769 | |
| rMOMP + ADJ.B | 558090 | 1079692 | 42735 | 66320 | 364335 | 1025443 | 80% | 568 | 0.602 |

TABLE 20

| | MSD Analysis | | | | | | | |
|---|---|---|---|---|---|---|---|---|
| | INFγ | IL-10 | IL-4 | IL-5 | IL-2 | IL-12 | IL-13 | IL-17 |
| rMOMP + ADJ.SQ | 4885.8 | 11953.1 | 90.5 | 5670.6 | 575.8 | 219.3 | 3131.2 | 255.6 |
| rMOMP + Alum | 9981.9 | 3038.8 | 113.2 | 2789.8 | 582.2 | 282.0 | 1879.9 | 130.3 |
| rMOMP + ADJ.A | 20189.4 | 3626.1 | 72.7 | 1104.1 | 2934.0 | 438.8 | 2662.0 | 346.9 |
| rMOMP + ADJ.B | 15869.9 | 766.3 | 77.7 | 1006.2 | 4832.4 | 395.4 | 4461.1 | 922.8 |

These results demonstrated that rMOMP adjuvanted with E6020 irrespective of the carrier system used (i.e., either aluminum or emulsion) induces a Th1/Th2 balanced response whereas a Th2-orientated immune response is induced by rMOMP adjuvanted with the carrier system alone (e.g., Alum).

What we claim is:
1. An immunogenic composition comprising:
   a) purified Chlamydial major outer membrane protein or an immunogenic fragment thereof from at least one Chlamydial serovar, and;
   b) a thermoreversible emulsion comprising E6020 having the formula squalene, a polyoxyethylene alkyl ether, a hydrophobic nonionic surfactant, mannitol and an aqueous solvent; wherein the immunogenic composition:
   comprises about 2.5% squalene; and,
   upon administration to a mammal, induces neutralizing antibodies against *C. trachomatis* in the mammal as determined by an in vitro neutralization assay.

2. The composition of claim 1, further comprising an aluminum salt.

3. The composition of claim 2 wherein the aluminum salt is aluminum hydroxide.

4. The composition according to claim 1, further comprising at least one immunostimulant.

5. The composition of claim 4, wherein the immunostimulant is a Toll-like receptor 7/8 agonist.

6. The composition of claim 1, wherein the major outer membrane protein is from at least one serovar of *Chlamydia trachomatis*.

7. The composition of claim 6, wherein the major outer membrane protein is selected from *C. trachomatis* serovars: E, D, F, G, H, I, J, K, L1, L2, and L3.

8. The composition of claim 7 wherein the major outer membrane protein is from serovar E.

9. The composition of claim 6, comprising at least three major outer membrane proteins from *C. trachomatis*, each selected from serovars: E, D, F, G, H, I, J, K, L1, L2, and L3.

10. The composition of claim 9, wherein the composition comprises three *C. trachomatis* major outer membrane proteins, one from serovar E, one from serovar D and one from serovar F.

11. The composition according to claim 1 wherein the major outer membrane protein is recombinantly derived.

12. The immunogenic composition of claim 1 wherein the polyoxyethylene alkyl ether is selected from the group consisting of ceteareth-12, ceteareth-20, steareth-21, ceteth-20, ceteth-10, steareth-10, steareth-20, oleth-10, and oleth-20.

13. The immunogenic composition of claim 12 wherein the polyoxyethylene alkyl ether is ceteth-10.

14. The immunogenic composition of claim 12 wherein the polyoxyethylene alkyl ether is ceteareth-12.

15. The immunogenic composition of claim 14 wherein the hydrophobic nonionic surfactant is sorbitan monoleate.

16. The immunogenic composition of claim 1 wherein the hydrophobic nonionic surfactant is a sorbitan ester or a mannide ester.

17. The immunogenic composition of claim 1 wherein the polyoxyethylene alkyl ether is ceteareth-12 and the hydrophobic nonionic surfactant is sorbitan monoleate.

* * * * *